US011447577B2

(12) United States Patent
Kulkarni et al.

(10) Patent No.: US 11,447,577 B2
(45) Date of Patent: *Sep. 20, 2022

(54) CYCLODEXTRIN BASED POLYMERS, METHODS, COMPOSITIONS AND APPLICATIONS THEREOF

(71) Applicant: ATEN PORUS LIFESCIENCES, Bangalore (IN)

(72) Inventors: Aditya Kulkarni, Bangalore (IN); Atul Dolas, Bangalore (IN); Princy Khurana, Bangalore (IN); Soniya Johny, Bangalore (IN); Manu Manjunath, Bangalore (IN)

(73) Assignee: Aten Porus Lifesciences, Bangalore (IN)

( * ) Notice: Subject to any disclaimer, the term of this patent is extended or adjusted under 35 U.S.C. 154(b) by 818 days.

This patent is subject to a terminal disclaimer.

(21) Appl. No.: 16/071,782

(22) PCT Filed: Jan. 20, 2017

(86) PCT No.: PCT/IB2017/050309
§ 371 (c)(1),
(2) Date: Jul. 20, 2018

(87) PCT Pub. No.: WO2017/125889
PCT Pub. Date: Jul. 27, 2017

(65) Prior Publication Data
US 2021/0102006 A1    Apr. 8, 2021

(30) Foreign Application Priority Data

Jan. 21, 2016 (IN) .............................. 201641002350

(51) Int. Cl.
C08B 37/16     (2006.01)
A61K 47/61     (2017.01)
A61K 47/55     (2017.01)
A61P 3/00      (2006.01)

(52) U.S. Cl.
CPC .......... *C08B 37/0012* (2013.01); *A61K 47/55* (2017.08); *A61K 47/61* (2017.08); *A61P 3/00* (2018.01)

(58) Field of Classification Search
CPC .. C08B 37/0012; A61K 31/724; A61K 47/61; A61K 47/6951
See application file for complete search history.

(56) References Cited

U.S. PATENT DOCUMENTS

2002/0151523 A1* 10/2002 Davis ..................... C08G 69/40
                                                       514/58
2012/0004195 A1    1/2012  Glucksmann et al.
2014/0213504 A1    7/2014  Fetzer et al.

FOREIGN PATENT DOCUMENTS

WO   WO 2006/089007 A2   8/2006
WO   WO 2014/022841 A1   2/2014
WO   WO 2017/006279 A1   1/2017

OTHER PUBLICATIONS

Christensen, H. et al "Recognition of peptides by cyclodextrin trimers" Eur. J. Org. Chem., vol. 2011, issue 27, pp. 5279-5290. (Year: 2011).*
International Search Report and Written Opinion issued by the International Searching Authority for Application No. PCT/IB2017/050309, dated Apr. 5, 2017, 15 pages.
Tamura et al., Lysosomal-specific Cholesterol Reduction by Biocleavable Polyrotaxanes for Ameliorating Niemann-Pick Type C Disease, Scientific Reports 4:4356/1-4356/8 (2014).
Cheng et al., "Synthesis of linear, beta-cyclodextrin-based polymers and their camptothecin conjugates", Bioconjugate Chemistry 14(5):1007-1017 (2003).
Collins et al., "Synthesis, Characterization, and Evaluation of Pluronic-Based [beta]-Cyclodextrin Polyrotaxanes for Mobilization of Accumulated Cholesterol from Niemann-Pick Type C Fibroblasts", Biochemistry, 52(19):3242-3253 (2013).
Szente, L. & Szejtli, J., "Highly soluble cyclodextrin derivatives: chemistry, properties, and trends in development," Adv. Drug Deliv. Rev. 36:17-28 (1999).
Kilsdonk et al., "Cellular cholesterol efflux mediated by cyclodextrins," J. Biol. Chem. 270(29):17250-17256 (1995).
Peake et al., "Normalization of cholesterol homeostasis by 2-hydroxypropyl-ß-cyclodextrin in neurons and glia from Niemann-Pick C1 (NPC1)-deficient mice," J. Biol. Chem. 287:9290-9298 (2012).
Lopez et al., "Systemic administration of 2-hydroxypropyl-β-cyclodextrin to symptomatic Npc1-deficient mice slows cholesterol sequestration in the major organs and improves liver function," Clin Exp Pharmacol Physiol. 41:780-787 (2014).
Taylor et al., "Cyclodextrin mediates rapid changes in lipid balance in Npc1$^{-/-}$ mice without carrying cholesterol through the bloodstream," J Lipid Res. 53:2331-2342 (2012).
Davidson et al., "Efficacy and ototoxicity of different cyclodextrins in Niemann-Pick C disease," Ann. Clin. Trans. Neurol. 3:366-380 (2016).
Camargo et al., "Cyclodextrins in the treatment of a mouse model of Niemann-Pick C disease," Life Sci. 70:131-142 (2001).
Ramirez et al., "Weekly cyclodextrin administration normalizes cholesterol metabolism in nearly every organ of the Niemann-Pick type C1 mouse and markedly prolongs life," Pediatr. Res. 68:309-315 (2010).

(Continued)

*Primary Examiner* — Leigh C Maier
(74) *Attorney, Agent, or Firm* — Cooley LLP

(57) ABSTRACT

The present disclosure relates to polymers comprising conjugates of cyclodextrin or derivatives thereof and a linker moiety, methods of preparing the same and their application in the removal of lipids such as cholesterol from cells in treating lipid storage disorders. The present polymers exhibit improved properties including but not limiting to improved biocompatibility, improved retention time, prolonged duration of action in cells, and increased efficacy in removal of cholesterol from cells in treating lipid storage disorders.

20 Claims, 35 Drawing Sheets

(56) References Cited

OTHER PUBLICATIONS

Davidson et al., "Chronic cyclodextrin treatment of murine Niemann-Pick C disease ameliorates neuronal cholesterol and glycosphingolipid storage and disease progression," Plos One 4, e6951 (2009), 15 pages.

Vite et al., "Intracisternal Cyclodextrin Prevents Cerebellar Dysfunction and Purkinje Cell Death in Feline Niemann-Pick type C1 disease," Sci. Transl. Med. 7(276):276ra26 (2015), 35 pages.

Maarup et al. "Intrathecal 2-hydroxypropyl-β-cyclodextrin in a single patient with Niemann-Pick C1," Mol. Genet. Metab. 116:75-79 (2015).

Ory et al., "Intrathecal 2-hydroxypropyl-β-cyclodextrin decreases neurological disease progression in Niemann-Pick disease, type C1: a non-randomised, open-label, phase 1-2 trial," Lancet. Oct. 14, 2017;390(10104):1758-1768.

Pontikis et al., Cyclodextrin alleviates neuronal storage of cholesterol in Niemann-Pick C disease without evidence of detectable blood-brain barrier permeability, J Inherit Metab Dis. 36:491-498 (2013).

Tanaka et al., "Efficacy of 2-hydroxypropyl-β-cyclodextrin in Niemann-Pick disease type C model mice and its pharmacokinetic analysis in a patient with the disease," Biol. Pharm. Bull. 38:844 851 (2015).

Mondjinou et al., "Synthesis of 2-hydroxypropyl-β-cyclodextrin/Pluronic-based polyrotaxanes via heterogeneous reaction as potential Niemann-Pick Type C therapeutics," Biomacromolecules. 14:4189-4197 (2013).

Tamura, A. & Yui, N., "β-Cyclodextrin-threaded biocleavable polyrotaxanes ameliorate impaired autophagic flux in Niemann-Pick type C disease," J Biol Chem. 290:9442-9454 (2015).

Alam et al., "Chronic administration of an HDAC inhibitor treats both neurological and systemic Niemann-Pick type C disease in a mouse model," Sci Transl Med. 8, 326ra23 (2016), 12 pages.

Brown et al., "PEG-lipid micelles enable cholesterol efflux in Niemann-Pick type C1 disease-based lysosomal storage disorder," Sci Rep. 6, 31750 (2016), 15 pages.

Lee et al., Polyketal microparticles: a new delivery vehicle for superoxide dismutase,. Bioconjug Chem. 18:4-7 (2007).

Maity et al., "A biodegradable adamantane polymer with ketal linkages in its backbone for gene therapy," Chem Commun (Camb). 51, 15956-15959 (2015).

* cited by examiner

R=H, β-Cyclodextrin;
R=CH₂CH(OH)CH₃, Hydroxy propyl β-Cyclodextrin;

wherein n ranges from 6 to 750.

▲ Polymer A (0.8 mg/g body weight) injection

▲ Polymer A (0.8 mg/g body weight) injection

□ wt (PN45 and PN60 groups were pooled)

■ $Npc1^{nmf164/nmf164}$ (PN45 and PN60 groups were pooled)

▲ Polymer A (0.8 mg/g body weight) injection

▲ Polymer A (0.8 mg/g body weight) injection

□ wt (PN45 and PN60 groups were pooled)

■ $Npc1^{nmf164/nmf164}$ (PN45 and PN60 groups were pooled)

CYCLODEXTRIN BASED POLYMERS, METHODS, COMPOSITIONS AND APPLICATIONS THEREOF

PRIORITY INFORMATION

This application is a U.S. National Phase application, filed under 35 U.S.C. § 371, of International Application No. PCT/IB2017/050309, filed on Jan. 20, 2017, which claims the benefit of Indian Provisional Patent Application No. 201641002350, filed Jan. 21, 2016, the contents of each of which are incorporated herein by reference in their entireties for all purposes.

TECHNICAL FIELD

The present disclosure is in the field of biomedical, pharmaceutical and polymeric sciences. The present disclosure relates macromolecular therapeutic agents, methods of making the same, and the therapeutic uses of the same in the treatment of various disorders including lipid storage disorders. In certain specific embodiments, the disclosure relates to polymers comprising conjugates of cyclodextrins, a salt thereof, a solvate thereof, and/or cyclodextrin derivatives, methods of making the same, and their use as therapeutic agents in the treatment of various disorders, for example removing excess lipids such as cholesterol from cells and/or treating lipid storage disorders.

BACKGROUND

Lipid storage diseases, or the lipidoses, are a group of metabolic disorders in which harmful or excessive amounts of lipids (e.g., cholesterol) accumulate in various cells and tissues in the body. Patients with these disorders typically exhibit elevated levels of cholesterol in various tissues of the body, as these patients either do not produce adequate quantities of one or more enzymes needed to metabolize lipids or they produce enzymes that do not work properly. In recent years, sedentary life styles and poor diet habits of people are also factors leading to lipid disorders.

Niemann-Pick type C disorder (NPC) is a lysosomal storage disorder disease caused by accumulation of unesterified cholesterol and sphingolipids in the lysosomes of brain, liver, spleen, and lung cells. Aberrant accumulation of cholesterol in NPC cells has been shown to originate from mutation of genes encoding either the membrane-bound NPC1 proteins or the soluble NPC2 proteins required for cholesterol efflux from the lysosome. Unfortunately, the treatment options are limited for this typically fatal disease.

No significant therapeutic benefit has been achieved by reducing cholesterol storage by treating with dietary reduction or knock-out of Low Density lipoprotein receptors. There has been extensive research aimed at identifying a reliable cure or preventive measures for lipid storage disorders including NPC. Chaperone-based therapy, gene therapy and recombinant enzyme therapies are some of the important therapeutic regimens attempted in this area for treating lipid storage disorders including NPC, which is still in various stages of development. Furthermore, some benefit has been reported in a clinical trial using Miglustat (OGT 918, N-butyl-deoxynojirimycin) but currently no clinically approved cure exists for lipid storage disorders, especially Niemann-Pick Type C disorder.

Hydrophilic molecules, such as cyclodextrin, which are generally employed to treat lipid storage disorders, undergo rapid clearance from the bloodstream due to their high water solubility. Therefore, to maintain a minimum effective concentration of a therapeutic drug, usually high concentrations/doses or repeated administration of these hydrophilic drugs are required to be administered to the subject. Administration of higher concentrations/doses of any therapeutic agent/drug to the subject may lead to toxicity and adverse effects to various organs of the subject. Thus, such therapeutic agents suffer drawbacks stemming from rapid clearance from the body. Hence, balancing the clearance rate of these therapeutic agents and maintaining the minimum effective concentration of these drugs in the desired site or organ without compromising the efficacy of the drug is a critical objective in the development of drugs and drug delivery systems.

Accordingly, there has been a continuing need in the art to provide drugs/drug-polymer conjugates having improved/greater efficacy along with prolonged duration of action for treating lysosomal lipid storage disorders including NPC. The present disclosure overcomes the aforesaid drawbacks of the prior art.

SUMMARY OF THE DISCLOSURE

The polymers of the present disclosure can be useful for treating a condition or a disease associated with abnormal NPC1 and/or NPC2 protein production, such as lysosomal lipid storage disorders. In one embodiment, the present disclosure provides polymers comprising the following structure:

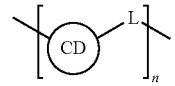

wherein the polymer comprises a product obtained by reacting CD and L;
CD is a cyclodextrin moiety, or a derivative thereof;
L is a linker moiety; and
n is from 4 to 1000.

In one embodiment, the cyclodextrin moiety is selected from α-cyclodextrin, β-cyclodextrin, γ-cyclodextrin, derivatives thereof, or combinations thereof. In some embodiments, the cyclodextrin moiety, or a derivative thereof is derived from hydroxyalkyl-α-cyclodextrin, hydroxyalkyl-β-cyclodextrin, hydroxyalkyl-γ-cyclodextrin, derivatives thereof, or combinations thereof. By "derived" from a particular indicated cyclodextrin or cyclodextrin derivative, etc., we mean the cyclodextrin moiety and linker moiety result from the reaction of the indicated cyclodextrin or cyclodextrin derivative with a linking agent, thereby providing a polymeric compound of the present invention. In other embodiments, the cyclodextrin or derivative thereof is β-cyclodextrin, (2-hydroxypropy)-β-cyclodextrin, derivatives thereof, or combinations thereof. In one embodiment, the cyclodextrin is β-cyclodextrin or (2-hydroxypropy)-β-cyclodextrin.

In one embodiment, the cyclodextrin moiety is derived from a hydroxyalkyl-α-cyclodextrin, hydroxyalkyl-β-cyclodextrin, hydroxyalkyl-γ-cyclodextrin, or derivatives thereof. In various embodiments, the alkyl group of such cyclodextrins is selected from $C_1$-$C_{10}$ linear alkyl, $C_1$-$C_{10}$ branched alkyl or $C_1$-$C_{10}$ cycloalkyl, each are optionally substituted. In some embodiment, the optional substituent for alkyl is selected from methyl, ethyl or butyl.

In one embodiment, L comprises the following structure:

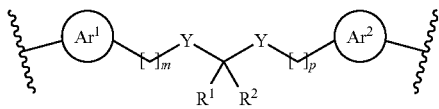

wherein $Ar^1$ and $Ar^2$ are each independently a 5- or 6-membered heteroaryl comprising 1, 2, 3 or 4 heteroatoms individually selected from N, O, and S, wherein $A^1$ and $Ar^2$ are optionally substituted with $R^3$;

Y is independently O, S, or $NR^4$;

m and p are each independently an integer from 1 to 10;

$R^1$ and $R^2$ are each independently $R^4$, $OR^4$, S or $R^1$ and $R^2$ together form a double bonded O, S, or $NR^4$, each of which are optionally substituted; and $R^3$ is selected from $C_1$-$C_3$ alkyl, $C_1$-$C_3$ alkyl sulphide, hydrazone, amine, and halogen.

In one embodiment, Y is O.

In one embodiment, m and p are both 1.

In one embodiment, $R^1$ and $R^2$ are each C1-C3 alkyl.

In one embodiment, wherein $R^1$ and $R^2$ are each methyl.

In one embodiment, wherein $A^1$ and $Ar^2$ are each triazole.

In one embodiment, wherein $A^1$ and $Ar^2$ are the same heteroaryl.

In one embodiment, L is

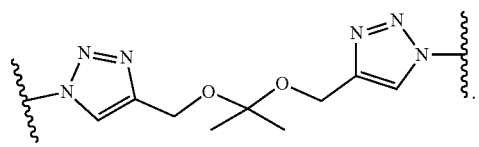 [SMILES: *n1cc(COC(C)(C)OCc2cn(*)nn2)nn1]

In one embodiment, the polymer of the present disclosure has the following structure:

to 250. In one embodiment, n is from 10 to 300. In one embodiment, n is from 10 to 100. In one embodiment, n is from 10 to 75. In one embodiment, n is from 15 to 65. In one embodiment, n is from 20 to 30. In one embodiment, n is from 50 from 65.

In one embodiment of the present disclosure, a pharmaceutical composition is provided comprising a pharmaceutically acceptable carrier or a pharmaceutical excipient and a polymer of the present disclosure, e.g., polymers comprising conjugates of cyclodextrins. In another embodiment, the pharmaceutical composition disclosed herein further comprises a therapeutically active agent.

In one embodiment of the present disclosure, a method of treating a disease or a condition associated with abnormal NPC1 and/or NPC2 protein production is provided, comprising administering to a subject in need thereof a polymer of the present disclosure, e.g., polymers comprising conjugates of cyclodextrins.

In one embodiment of the present disclosure, a method of treating lipid storage disorder is provided comprising administering to a subject in need thereof a polymer of the present disclosure, e.g., polymers comprising conjugates of cyclodextrins.

In one embodiment of the present disclosure, a method of removing excess lipid from a cell is provided comprising administering to a subject in need thereof a polymer of the present disclosure, e.g., polymers comprising conjugates of cyclodextrins.

In one embodiment, the polymer of the present disclosure has a polydispersity index of from about 1 to about 1.5.

In one embodiment, the polymer of the present disclosure has a polydispersity index of from about 1 to about 1.6.

In one embodiment, the polymer of the present disclosure has a polydispersity index of from about 1 to about 1.7.

In one embodiment, the polymer of the present disclosure has a polydispersity index of from about 1 to about 1.8.

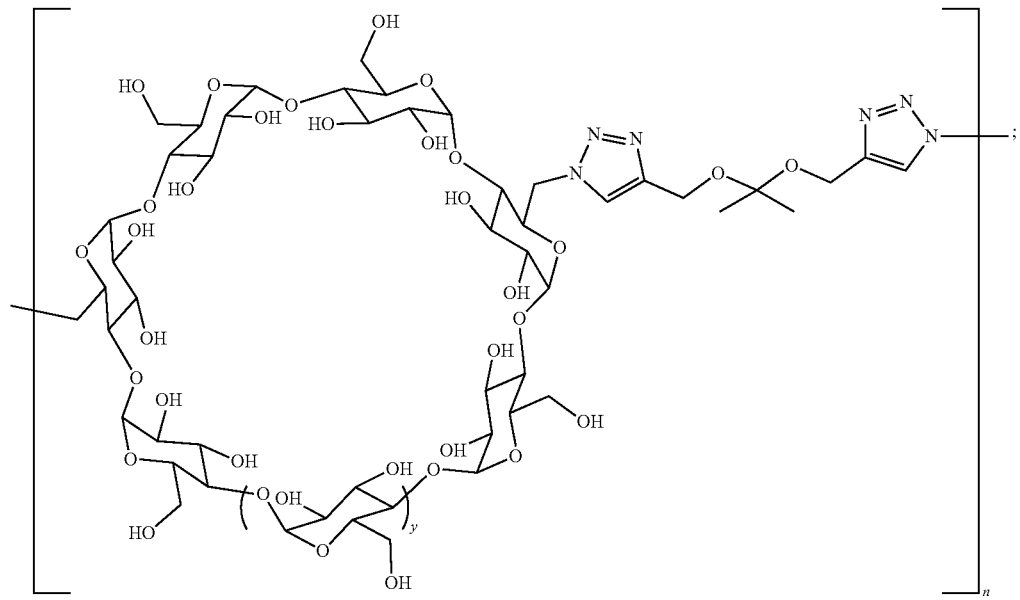

wherein n is as defined previously.

In one embodiment, n is from 10 to 150. In one embodiment, n is from 10 to 200. In one embodiment, n is from 10

In one embodiment, the polymer of the present disclosure has an elimination half-life of from about 6 hours to about 24 hours.

In one embodiment, the bioavailability of a therapeutically active agent administered with a polymer of the present disclosure is improved.

In one embodiment, permeation of the blood-brain barrier of a therapeutically active agent is improved by administering it with a polymer of the present disclosure.

C—shows motor behaviour assessment (balance beam test) for the WT and Npc1$^{nih}$ mice groups treated with Polymer A (0.4 mg/g, weekly injections starting at PN7). Polymer A treatments stabilize Npc1$^{nih}$ mouse weight loss, and delay the onset of ataxic symptoms.

Figure 25:
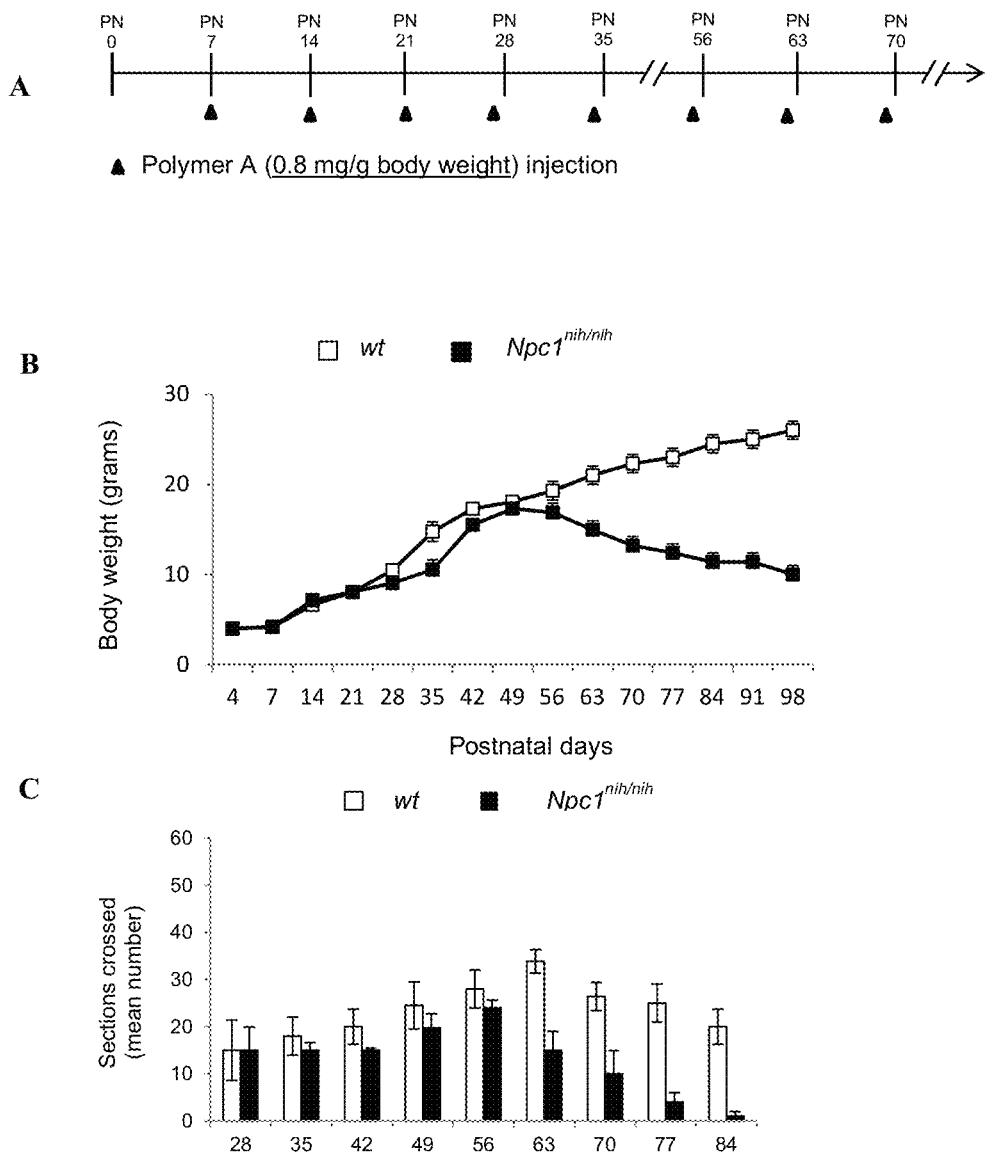

FIG. 25 shows the results of an experiment measuring the body weight and motor skills of WT and Npc1$^{nih}$ mice. A—shows dosing regimen of Polymer A (0.8 mg/g, weekly injections starting at PN7) in the efficacy studies in Npc1$^{nih}$ mice. B—shows body weight of the WT and Polymer A (0.8 mg/g, weekly injections starting at PN7) Npc1$^{nih}$ groups. C—shows motor behaviour assessment (balance beam test) for the WT and Npc1$^{nih}$ mice groups treated with Polymer A (0.8 mg/g, weekly injections starting at PN7). Polymer A treatments stabilize Npc1$^{nih}$ mouse weight loss, and delay the onset of ataxic symptoms.

Figure 26:
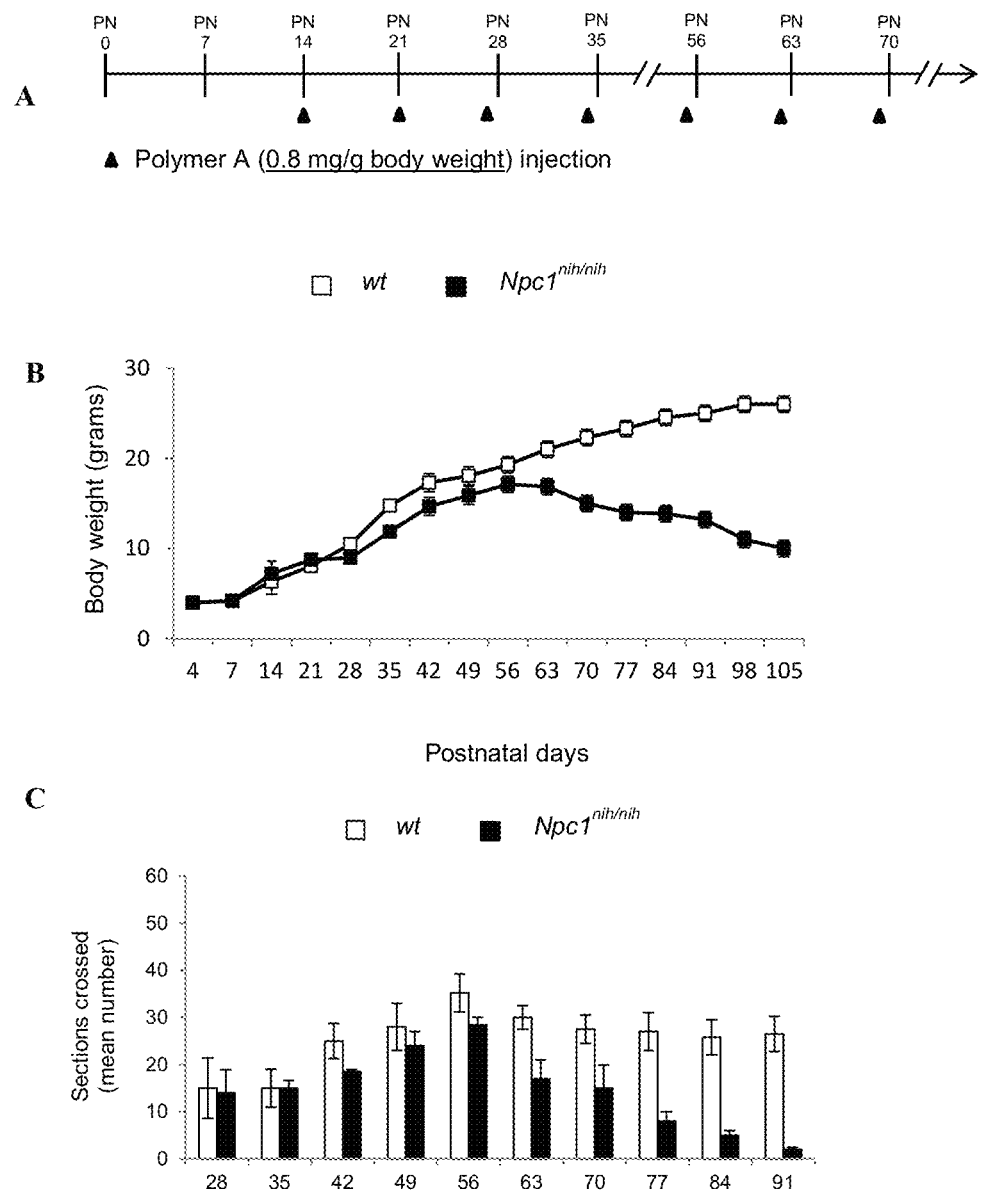

FIG. 26 shows the results of an experiment measuring the body weight and motor skills of WT and Npc1$^{nih}$ mice. A—shows dosing regimen of Polymer A (0.8 mg/g, weekly injections starting at PN14) in the efficacy studies in Npc1$^{nih}$ mice. B—shows body weight of the WT and Polymer A (0.8 mg/g, weekly injections starting at PN14) Npc1$^{nih}$ groups. C—shows motor behaviour assessment (balance beam test) for the WT and Npc1$^{nih}$ mice groups treated with Polymer A (0.8 mg/g, weekly injections starting at PN14). Polymer A treatments stabilize Npc1$^{nih}$ mouse weight loss, and delay the onset of ataxic symptoms.

Figure 27:
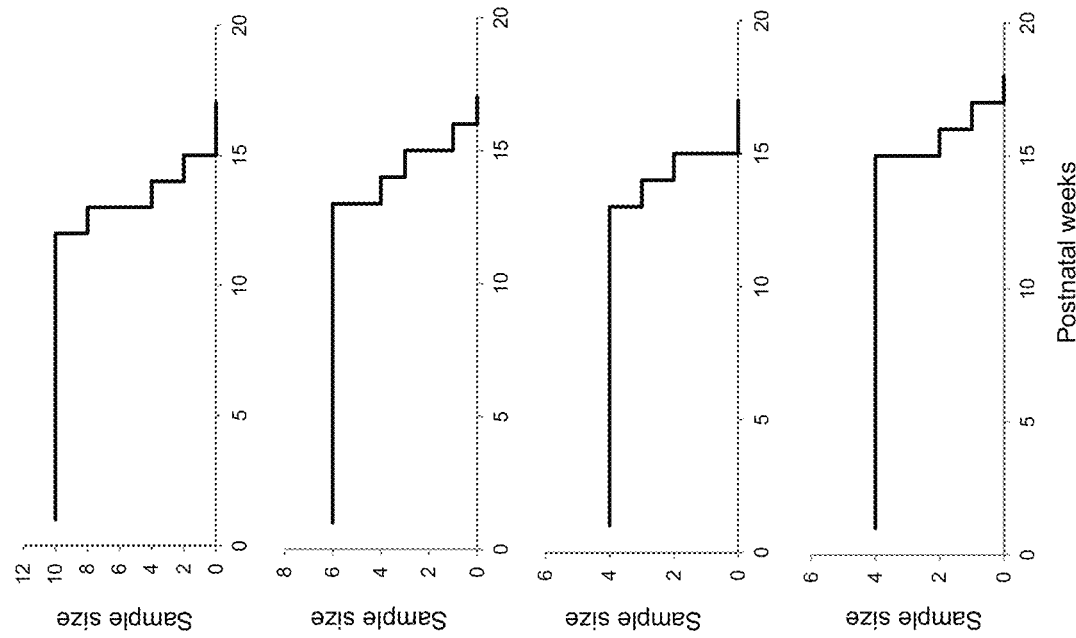
Figure 27:
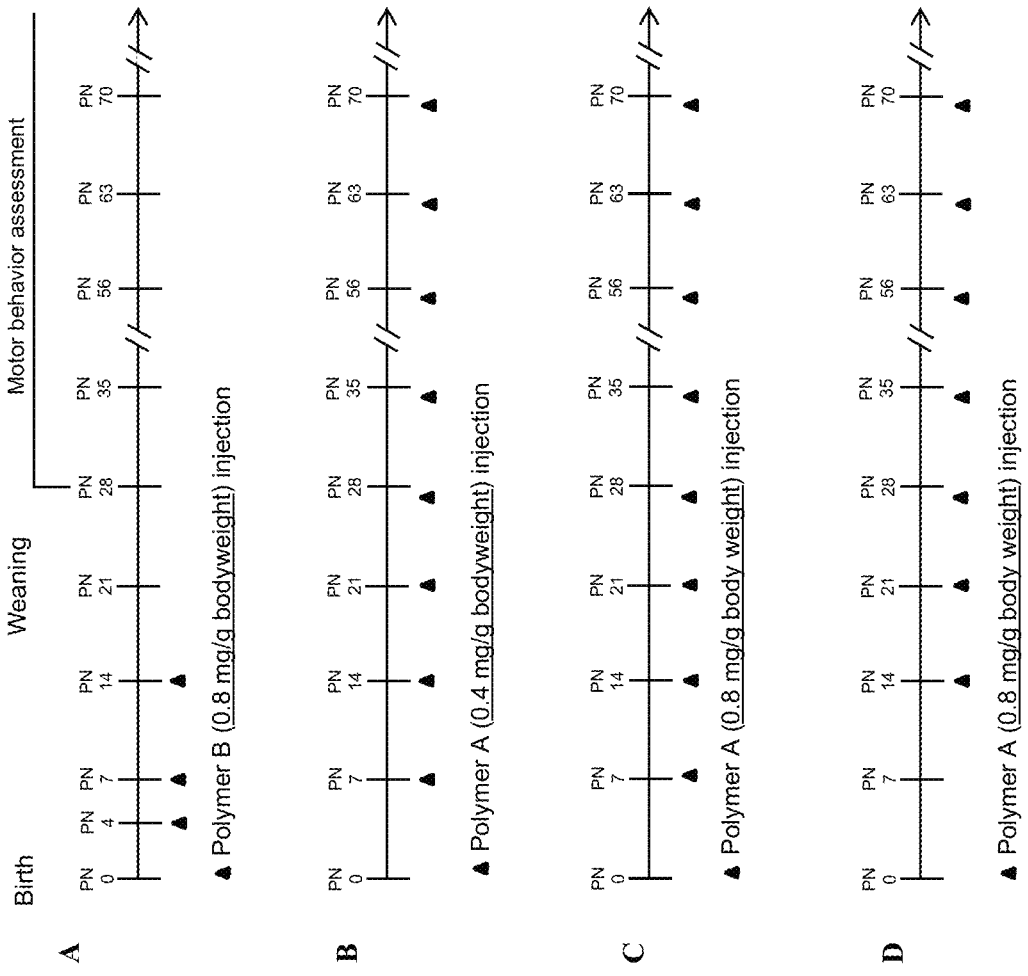

FIG. 27 shows survival rate of the Npc1$^{nih}$ mice under different treatments. A—shows survival rate of Npc1$^{nih}$ mice under Polymer B (0.8 mg/g, injections at PN4, PN7, and PN14) treatment. B—shows survival rate or Npc1$^{nih}$ mice under Polymer A (0.4 mg/g, weekly injections starting at PN7) treatment. C—shows survival rate or Npc1$^{nih}$ mice under Polymer A (0.8 mg/g, weekly injections starting at PN7) treatment. D—shows survival rate or Npc1$^{nih}$ mice under Polymer A (0.8 mg/g, weekly injections starting at PN14) treatment.

Figure 28:
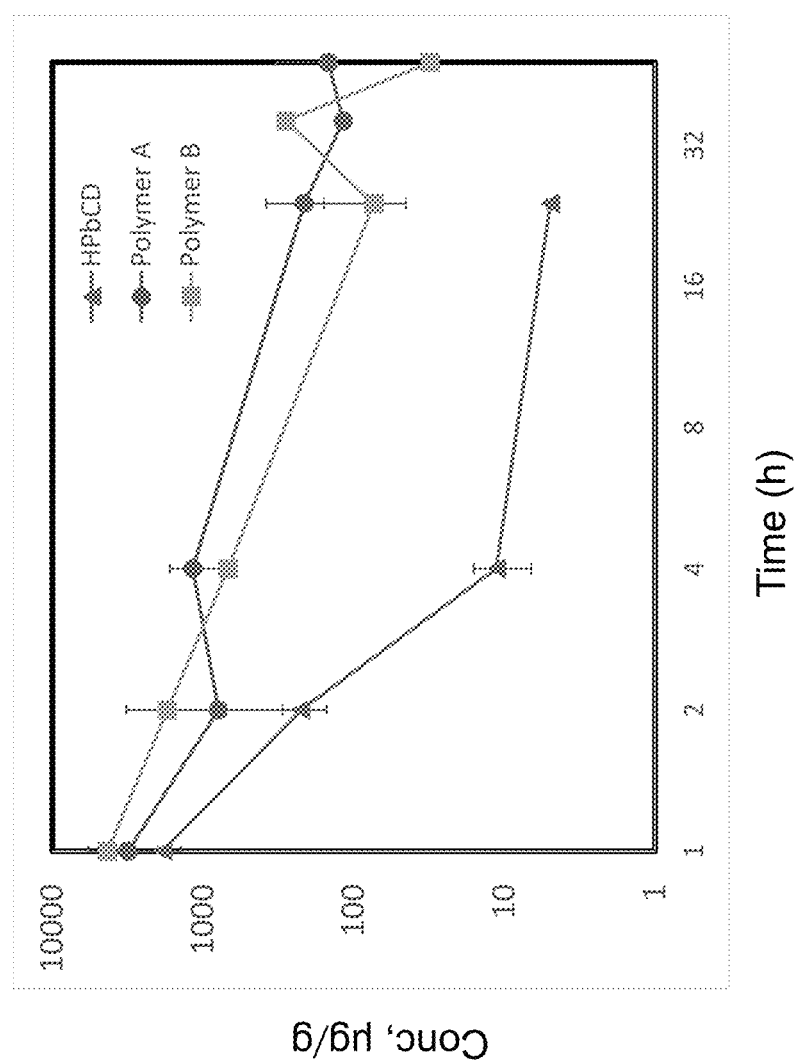

FIG. 28 shows the half-life of HPbCD compared to Polymer A and Polymer B. Error bars are SEM. Polymers A and B both exhibit significantly improved tissue half-lives compared to traditional HPbCD treatments.

DETAILED DESCRIPTION OF THE DISCLOSURE

Definitions

While the following terms are believed to be well understood by one of ordinary skill in the art, the following definitions are set forth to facilitate explanation of the presently disclosed subject matter.

Throughout the present specification, the terms "about" and/or "approximately" may be used in conjunction with numerical values and/or ranges. The term "about" is understood to mean those values near to a recited value. For example, "about 40 [units]" may mean within ±25% of 40 (e.g., from 30 to 50), within ±20%, ±15%, ±10%, ±9%, ±8%, ±7%, ±6%, ±5%, ±4%, ±3%, ±2%, ±1%, less than ±1%, or any other value or range of values therein or therebelow. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The term "a" or "an" refers to one or more of that entity; for example, "a kinase inhibitor" refers to one or more kinase inhibitors or at least one kinase inhibitor. As such, the terms "a" (or "an"), "one or more" and "at least one" are used interchangeably herein. In addition, reference to "an inhibitor" by the indefinite article "a" or "an" does not exclude the possibility that more than one of the inhibitors is present, unless the context clearly requires that there is one and only one of the inhibitors.

As used herein, the verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "treating" means one or more of relieving, alleviating, delaying, reducing, reversing, improving, or managing at least one symptom of a condition in a subject. The term "treating" may also mean one or more of arresting, delaying the onset (i.e., the period prior to clinical manifestation of the condition) or reducing the risk of developing or worsening a condition.

An "effective amount" means the amount of a formulation according to the invention that, when administered to a patient for treating a state, disorder or condition is sufficient to effect such treatment. The "effective amount" will vary depending on the active ingredient, the state, disorder, or condition to be treated and its severity, and the age, weight, physical condition and responsiveness of the mammal to be treated. In the context of therapeutic or prophylactic applications, in some embodiments, the amount of a composition administered to the subject will depend on the type, degree, and severity of the disease and on the characteristics of the individual, such as general health, age, sex, body weight and tolerance to drugs. The skilled artisan will be able to determine appropriate dosages depending on these and other factors.

The term "therapeutically effective" applied to dose or amount refers to that quantity of a compound or pharmaceutical formulation that is sufficient to result in a desired clinical benefit after administration to a patient in need thereof.

All weight percentages (i.e., "% by weight" and "wt. %" and w/w) referenced herein, unless otherwise indicated, are measured relative to the total weight of the pharmaceutical composition.

As used herein, "substantially" or "substantial" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result. For example, a composition that is "substantially free of" other active agents would either completely lack other active agents, or so nearly completely lack other active agents that the effect would be the same as if it completely lacked other active agents. In other words, a composition that is "substantially free of" an ingredient or element or another active agent may still contain such an item as long as there is no measurable effect thereof.

The terms below, as used herein, have the following meanings, unless indicated otherwise:

"Amino" refers to the —NH$_2$ radical.

"Cyano" refers to the CN radical.

"Halo" or "halogen" refers to bromo, chloro, fluoro or iodo radical.

"Hydroxy" or "hydroxyl" refers to the OH radical.

"Imino" refers to the =NH substituent.

"Nitro" refers to the NO$_2$ radical.

"Oxo" refers to the =O substituent.

"Thioxo" refers to the =S substituent.

"Alkyl" or "alkyl group" refers to a fully saturated, straight or branched hydrocarbon chain radical having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for C1-C5 alkyls but also includes C6 alkyls. A C1-C10 alkyl includes all moieties described above for C1-C5 alkyls and C1-C6 alkyls, but also includes C7, C8, C9 and C10 alkyls. Similarly, a C1-C12 alkyl includes all the foregoing moieties, but also includes C11 and C12 alkyls. Non-limiting examples of C1-C12 alkyl include methyl, ethyl, n-propyl, i-propyl, sec-propyl, n-butyl, i butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n butylene, ethenylene, propenylene, n butenylene, propynylene, n butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain radical having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a C2-C12 alkenyl, an alkenyl comprising up to 10 carbon atoms is a C2-C10 alkenyl, an alkenyl group comprising up to 6 carbon atoms is a C2-C6 alkenyl and an alkenyl comprising up to 5 carbon atoms is a C2-C5 alkenyl. A C2-C5 alkenyl includes C5 alkenyls, C4 alkenyls, C3 alkenyls, and C2 alkenyls. A C2-C6 alkenyl includes all moieties described above for C2-C5 alkenyls but also includes C6 alkenyls. A C2-C10 alkenyl includes all moieties described above for C2-C5 alkenyls and C2-C6 alkenyls, but also includes C7, C8, C9 and C10 alkenyls. Similarly, a C2-C12 alkenyl includes all the foregoing moieties, but also includes C11 and C12 alkenyls. Non-limiting examples of C2-C12 alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkenylene" or "alkenylene chain" refers to a straight or branched divalent hydrocarbon chain radical, having from two to twelve carbon atoms, and having one or more carbon-carbon double bonds. Non-limiting examples of C2-C12 alkenylene include ethene, propene, butene, and the like. The alkenylene chain is attached to the rest of the molecule through a single bond and to the radical group through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain radical having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a C2-C12 alkynyl, an alkynyl comprising up to 10 carbon atoms is a C2-C10 alkynyl, an alkynyl group comprising up to 6 carbon atoms is a C2-C6 alkynyl and an alkynyl comprising up to 5 carbon atoms is a C2-C5 alkynyl. A C2-C5 alkynyl includes C5 alkynyls, C4 alkynyls, C3 alkynyls, and C2 alkynyls. A C2-C6 alkynyl includes all moieties described above for C2-C5 alkynyls but also includes C6 alkynyls. A C2-C10 alkynyl includes all moieties described above for C2-C5 alkynyls and C2-C6 alkynyls, but also includes C7, C8, C9 and C10 alkynyls. Similarly, a C2-C12 alkynyl includes all the foregoing moieties, but also includes C11 and C12 alkynyls. Non-limiting examples of C2-C12 alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain radical, having from two to twelve carbon atoms, and having one or more carbon-carbon triple bonds. Non-limiting examples of C2-C12 alkynylene include ethynylene, propargylene and the like. The alkynylene chain is attached to the rest of the molecule through a single bond and to the radical group through a single bond. The points of attachment of the alkynylene chain to the rest of the molecule and to the radical group can be through one carbon or any two carbons within the chain. Unless stated otherwise specifically in the specification, an alkynylene chain can be optionally substituted.

"Alkoxy" refers to a radical of the formula ORa where Ra is an alkyl, alkenyl or alkynyl radical as defined above containing one to twelve carbon atoms. Unless stated otherwise specifically in the specification, an alkoxy group can be optionally substituted.

"Alkylamino" refers to a radical of the formula —NHRa or —NRaRa where each Ra is, independently, an alkyl, alkenyl or alkynyl radical as defined above containing one to twelve carbon atoms. Unless stated otherwise specifically in the specification, an alkylamino group can be optionally substituted.

"Alkylcarbonyl" refers to the —C(=O)Ra moiety, wherein Ra is an alkyl, alkenyl or alkynyl radical as defined above. A non-limiting example of an alkyl carbonyl is the methyl carbonyl ("acetal") moiety. Alkylcarbonyl groups can also be referred to as "Cw-Cz acyl" where w and z depicts the range of the number of carbon in Ra, as defined above. For example, "C1-C10 acyl" refers to alkylcarbonyl group as defined above, where Ra is C1-C10 alkyl, C1-C10 alkenyl, or C1-C10 alkynyl radical as defined above. Unless stated otherwise specifically in the specification, an alkyl carbonyl group can be optionally substituted.

"Aryl" refers to a hydrocarbon ring system radical comprising hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Aralkyl" or "arylalkyl" refers to a radical of the formula —$R_b$-$R_c$ where $R_b$ is an alkylene group as defined above and Rc is one or more aryl radicals as defined above, for example, benzyl, diphenylmethyl and the like. Unless stated otherwise specifically in the specification, an aralkyl group can be optionally substituted.

"Aralkenyl" or "arylalkenyl" refers to a radical of the formula —$R_b$-$R_c$ where $R_b$ is an alkenylene o group as defined above and Rc is one or more aryl radicals as defined above. Unless stated otherwise specifically in the specification, an aralkenyl group can be optionally substituted.

"Aralkynyl" or "arylalkynyl" refers to a radical of the formula —$R_b$-$R_c$ where $R_b$ is an alkynylene group as defined above and Rc is one or more aryl radicals as defined above. Unless stated otherwise specifically in the specification, an aralkynyl group can be optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Carbocyclic rings include aryls and cycloalkyl. cycloalkenyl and cycloalkynyl as defined herein. Unless stated otherwise specifically in the specification, a carbocyclyl group can be optionally substituted.

"Cycloalkyl" refers to a stable non aromatic monocyclic or polycyclic fully saturated hydrocarbon radical consisting solely of carbon and hydrogen atoms, which can include fused or bridged ring systems, having from three to twenty carbon atoms, preferably having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7 dimethyl bicyclo[2.2.1]heptanyl, and the like. Unless otherwise stated specifically in the specification, a cycloalkyl group can be optionally substituted.

"Heterocyclyl," "heterocyclic ring" or "heterocycle" refers to a stable 3 to 20 membered non aromatic ring radical which consists of two to twelve carbon atoms and from one to six heteroatoms selected from the group consisting of nitrogen, oxygen and sulfur. Heterocyclyl or heterocyclic rings include heteroaryls as defined below. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2 oxopiperazinyl, 2 oxopiperidinyl, 2 oxopyrrolidinyl, oxazolidinyl, piperidinyl, piperazinyl, 4 piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1 oxo thiomorpholinyl, and 1,1 dioxo thiomorpholinyl. Unless stated otherwise specifically in the specification, a heterocyclyl group can be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group can be optionally substituted.

"Heteroaryl" refers to a 5 to 20 membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4 benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2 a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2 oxoazepinyl, oxazolyl, oxiranyl, 1-oxidopyridinyl, 1 oxidopyrimidinyl, 1-oxidopyrazinyl, 1-oxidopyridazinyl, 1 phenyl 1H pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group can be optionally substituted.

"Heteroarylalkyl" refers to a radical of the formula Rb-Rf where Rb is an alkylene chain as defined above and Rf is a heteroaryl radical as defined above. Unless stated otherwise specifically in the specification, a heteroarylalkyl group can be optionally substituted.

"Thioalkyl" refers to a radical of the formula —SRa where Ra is an alkyl, alkenyl, or alkynyl radical as defined above containing one to twelve carbon atoms. Unless stated otherwise specifically in the specification, a thioalkyl group can be optionally substituted.

The term "substituted" used herein means any of the above groups (i.e., alkyl, alkylene, alkenyl, alkenylene, alkynyl, alkynylene, alkoxy, alkylamino, alkylcarbonyl, thioalkyl, aryl, aralkyl, carbocyclyl, cycloalkyl, cycloalkenyl, cycloalkynyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$R$_h$, —NR$_g$C(═O)R$_h$, —NR$_g$C(═O)NR$_g$R$_h$, —NR$_g$C(═O)OR$_h$, —NR$_g$SO$_2$R$_h$, —OC(═O)NR$_g$R$_h$, —OR$_g$, —SR$_g$, —SOR$_g$, —SO$_2$R$_g$, —OSO$_2$R$_g$, —SO$_2$OR$_g$, ═NSO$_2$R$_g$, and —SO$_2$NR$_g$R$_h$. "Substituted" also means any of the above groups in which one or more hydrogen atoms are replaced with —C(═O)R$_g$, —C(═O)OR$_g$, —C(═O)NR$_g$R$_h$, —CH$_2$SO$_2$R$_g$, —CH$_2$SO$_2$NR$_g$R$_h$. In the foregoing, R$_g$ and R$_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the symbol

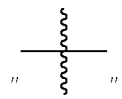

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

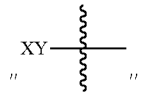

indicates that the chemical entity "XY" is bonded to another chemical entity via the point of attachment bond. Furthermore, the specific point of attachment to the non depicted chemical entity can be specified by inference. For example, the compound CH$_3$R$^3$, wherein R$^3$ is H or

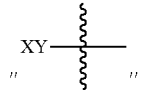

infers that when R$^3$ is "XY", the point of attachment bond is the same bond as the bond by which R$_3$ is depicted as being bonded to CH$_3$.

The following description includes information that may be useful in understanding the present invention. It is not an admission that any of the information provided herein is prior art or relevant to the presently claimed inventions, or that any publication specifically or implicitly referenced is prior art.

Cyclodextrin Polymers

The present disclosure is addressed to the aforementioned needs in the art and provides cyclodextrin based polymers/polymers of cyclodextrin conjugates and their applications in drug therapy. In an embodiment of the present disclosure, polymers of the present disclosure are useful as therapeutic agents for removing cholesterol from cells.

In one embodiment, the present disclosure relates to polymers of cyclodextrin conjugates.

The polymer of the present disclosure comprises repeating units of cyclodextrin moieties attached through a linkage. In an embodiment, the linkage is provided by a linker. In an embodiment, the linker is a covalent linker. In another embodiment, the linker is selected from a group comprising triazole, ketal and combinations thereof.

Figure 1:
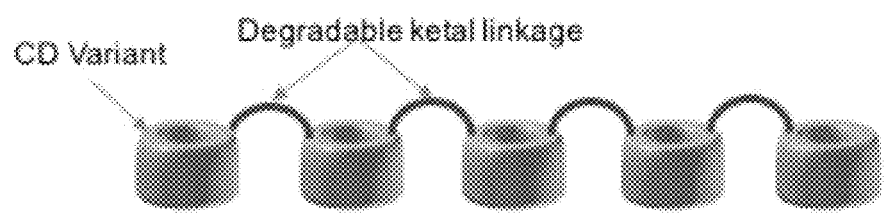
FIG. 1 is a drawing of the structure of an illustrative polymer comprising repeating units of cyclodextrin/cyclodextrin variants attached through linker moiety.
Figure 2:
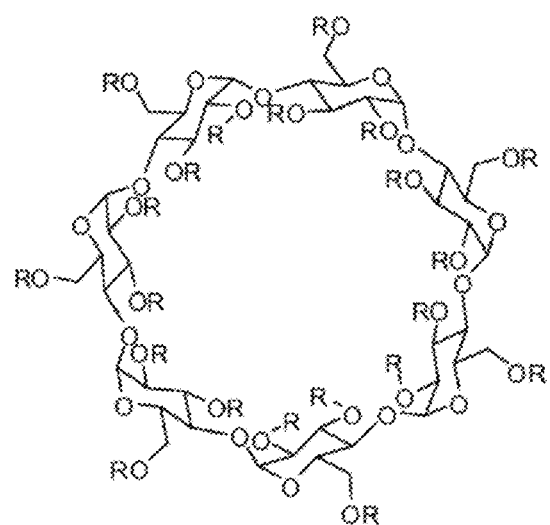
FIG. 2 depicts β-cyclodextrin (CD) and Hydroxypropyl-β-cyclodextrin (HP-β-CD).
Figure 3:
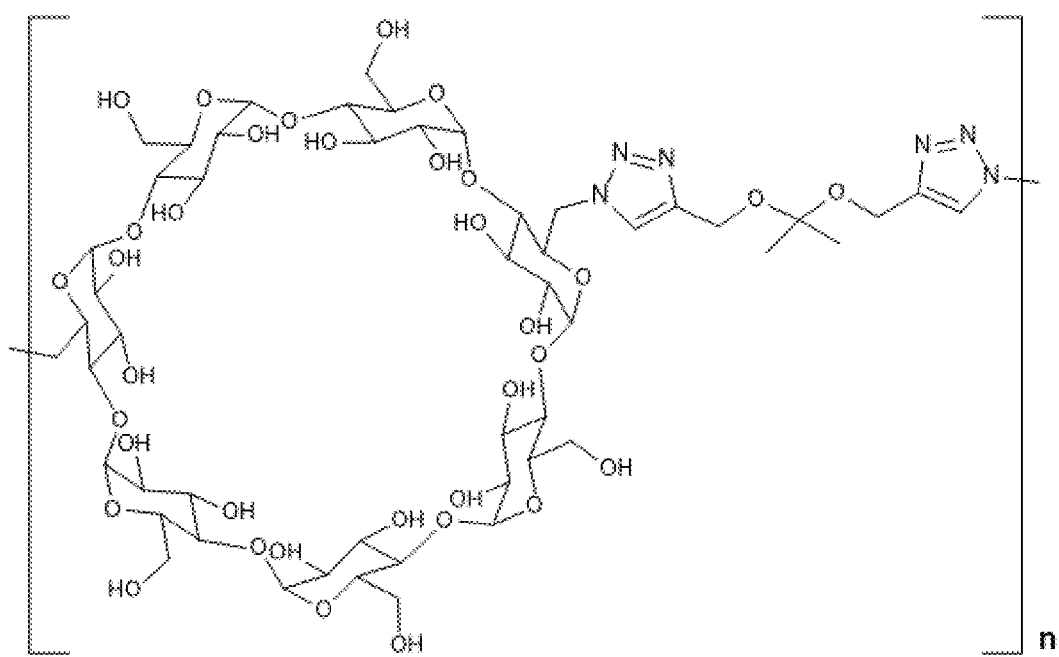
FIG. 3 depicts an exemplary pbCDK polymer structure (e.g., with repeating units of cyclodextrin-triazolyl-ketal-triazolyl) of present disclosure.

In one embodiment, the polymer of the present disclosure comprises repeating units of cyclodextrin moieties attached through a linker moiety. Thus, the polymer of the present disclosure may be represented as [-cyclodextrin-linker-]$_n$ (see, e.g., FIG. 1). In an exemplary embodiment, the linker moiety is triazole-ketal-triazole. Accordingly, in an exemplary embodiment, the polymer of the present disclosure is represented as [cyclodextrin-triazolyl-ketal-triazolyl]$_n$ (e.g., as shown in FIG. 3).

In a non-limiting embodiment, the cyclodextrin moiety in the polymer of the present disclosure includes but is not limited to β-cyclodextrin or its derivatives/variants, wherein the derivative/variants is selected from a group comprising α-cyclodextrin, Hydroxy propyl β-cyclodextrin (HP-β-CD), Sulfobutyl ether β-cyclodextrin (SBE-β-CD), Methyl β-cyclodextrin (Me-β-CD), γ-cyclodextrin, and other charged or uncharged derivatives of β-CD.

As used herein, the expressions "cyclodextrin based polymers", "polymers of cyclodextrin conjugates", "polymers comprising conjugates of cyclodextrins", "cyclodextrin: ketal conjugate", "cyclodextrin: ketal polymer", "cyclodextrin: ketal molecule", "conjugate of ketal with cyclodextrin", and "conjugate" are employed interchangeably within the instant disclosure and refer to the polymeric compound/therapeutic molecule/product of the instant disclosure.

The present disclosure particularly provides a polymer comprising a cyclodextrin-linker conjugate. In an embodiment of the present disclosure, the cyclodextrin-linker conjugate is a covalent conjugate.

In another embodiment of the present disclosure, the aforesaid polymer of cyclodextrin-linker conjugate comprises repeating units of β-cyclodextrin or its derivatives/variants conjugated through a covalent linker moiety. In a non-limiting embodiment of the present disclosure, the linker employed in the conjugate is a bio-degradable linker. In another embodiment, the linker moiety is selected from a group comprising triazole, ketal and a combination thereof. In other embodiments, the linker moiety is an ortho-ester, an acetal, a hydrazone, or a vinyl ether.

In one embodiment of the present disclosure, the linker is triazole-ketal-triazole moiety.

In another embodiment, the cyclodextrin derivative/variants is selected from a group comprising Hydroxy propyl β-cyclodextrin (HP-β-CD), Sulfobutyl ether β-cyclodextrin (SBE-β-CD), Methyl β-cyclodextrin (Me-β-CD), and other charged or uncharged derivatives of β-CD.

The present disclosure more particularly relates to polymers of cyclodextrin-triazole-ketal-triazole conjugates. In a non-limiting embodiment, the cyclodextrin includes but is not limited to β-cyclodextrin or its derivatives/variants, wherein the derivative/variants is selected from a group comprising Hydroxy propyl β-cyclodextrin (HP-β-CD), Sulfobutyl ether β-cyclodextrin (SBE-β-CD), Methyl β-cyclodextrin (Me-β-CD), and other charged or uncharged derivatives of β-CD.

The polymers of the present invention are long circulating, biocompatible, and can substantially increase cholesterol clearance from cells, specifically Niemann-Pick disease, type C (NPC) deficient cells. Further, the said polymers can deliver multiple copies/units of cyclodextrin or its derivatives/variants to the lysosomes of cells.

In an embodiment, the polymer of cyclodextrin conjugate (pbCDK) of the present disclosure is provided in FIG. 3, which can also be represented as [CD-triazolyl-ketal-triazolyl]$_n$, wherein n is an integer ranging from about 6 to 750.

In an embodiment, n is an integer ranging from about 50 to 150. In yet another embodiment, n is an integer ranging from about 50 to 500. In still another embodiment, n is an integer ranging from about 150 to 750. In one embodiment, n is an integer selected from 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 56, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 92, 94, 95, 96, 97, 98, or 100.

In one embodiment, the present disclosure provides a polymer comprising the following structure:

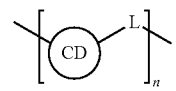

wherein the polymer comprises a product obtained by reacting CD and L; CD is a cyclodextrin moiety, a derivative thereof (such as an esterified cyclodextrin), a salt thereof, or a solvate thereof;
L is a linker moiety; and
n is from 4 to 1000.

In one embodiment, the cyclodextrin moiety or a derivative thereof, is selected from α-cyclodextrin, β-cyclodextrin, γ-cyclodextrin, derivatives thereof, salts thereof, or combinations thereof. In some embodiments, the cyclodextrin moiety or a derivative thereof is derived from the reaction of a cyclodextrin or cyclodextrin derivative such as a hydroxyalkyl-α-cyclodextrin, hydroxyalkyl-β-cyclodextrin, hydroxyalkyl-γ-cyclodextrin, derivatives thereof, or combinations thereof with a linker as described herein. In other embodiments, the cyclodextrin moiety or a derivative thereof, is derived from β-cyclodextrin, (2-hydroxypropy)-β-cyclodextrin, derivatives thereof, or combinations thereof. In one embodiment, the cyclodextrin is β-cyclodextrin or (2-hydroxypropy)-β-cyclodextrin.

In one embodiment, the alkyl in hydroxyalkyl-α-cyclodextrin, hydroxyalkyl-β-cyclodextrin, hydroxyalkyl-γ-cyclodextrin, derivatives thereof, a salt thereof, a solvate thereof, is selected from $C_1$-$C_{10}$ linear alkyl, $C_1$-$C_{10}$ branched alkyl or $C_1$-$C_{10}$ cycloalkyl, each are optionally substituted. In some embodiment, the optional substituent for alkyl is selected from methyl, ethyl and butyl.

In one embodiment, L comprises the following structure:

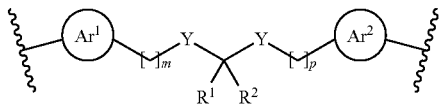

wherein $A^1$ and $Ar^2$ are each independently a 5- or 6-membered heteroaryl comprising 1, 2, 3 or 4 heteroatoms individually selected from N, O, and S, wherein $A^1$ and $Ar^2$ are optionally substituted with $R^3$;
Y is O, S, or $NR^4$;
m and p is each independently an integer from 1 to 10;
$R^1$ and $R^2$ are each independently $R^4$, $OR^4$, S or $R^1$ and $R^2$ together form a double bonded O, S, or $NR^4$; and
$R^3$ is selected from $C_1$-$C_3$ alkyl, $C_1$-$C_3$ alkyl sulphide, hydrazone, amine, and halogen.
$R^4$ is H or a saturated or unsaturated $C_1$-$C_{10}$ linear alkyl, saturated or unsaturated $C_1$-$C_{10}$ branched alkyl, or saturated or unsaturated $C_1$-$C_{10}$ cycloalkyl, each of which are optionally substituted.

In one embodiment, Y is O.

In one embodiment, m and p are each independently selected form 1, 2, 3, 4, or 5. In some embodiments, m and p are both 1.

In one embodiment, $R^1$ and $R^2$ are each $C_1$-$C_6$ alkyl. In some embodiment, $R^1$ and $R^2$ are each $C_1$-$C_3$ alkyl. In one embodiment $R^1$ and $R^2$ are each selected form methyl, ethyl, propyl, and isopropyl. In one embodiment, wherein $R^1$ and $R^2$ are each methyl.

In one embodiment, wherein $A^1$ and $Ar^2$ are each 5-membered heteroaryl comprising 2 or 3 heteroatoms. In one embodiment, wherein $A^1$ and $Ar^2$ are each 6-membered heteroaryl comprising 2 or 3 heteroatoms. In one embodiment, wherein $A^1$ and $Ar^2$ are each triazole.

In one embodiment, wherein $A^1$ and $Ar^2$ are the same heteroaryl.

In one embodiment, L is

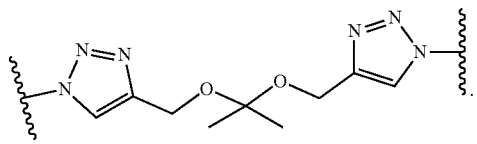 [SMILES: *n1cc(COC(C)(C)OCc2cn(*)nn2)nn1]

In one embodiment, the polymer of the present disclosure has the following structure:

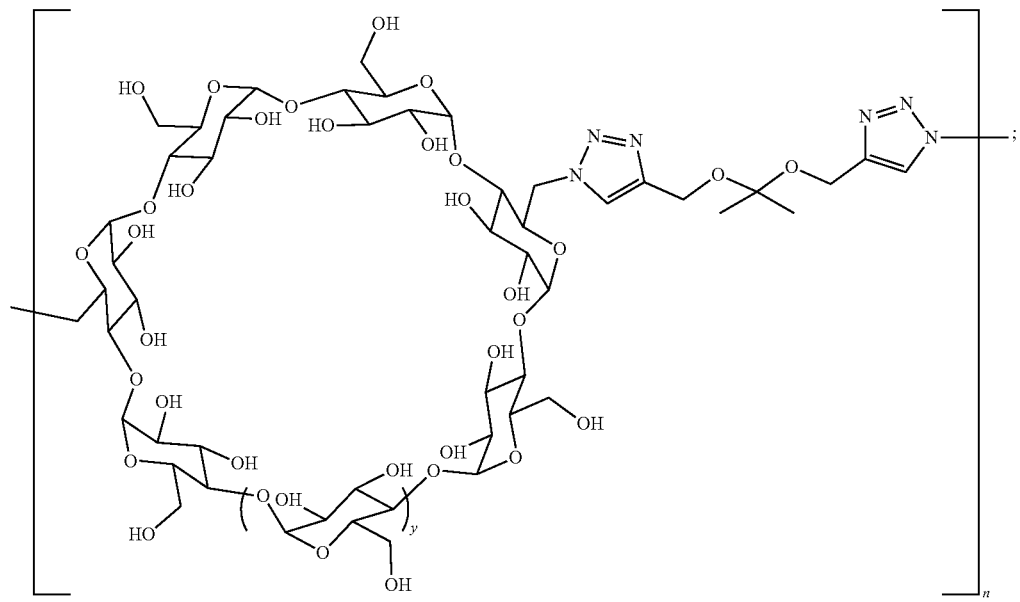

wherein n is as defined herein.

In one embodiment, n is from 10 to 100. In one embodiment, n is from 10 to 75. In one embodiment, n is from 15 to 65. In one embodiment, n is from 20 to 30. In one embodiment, n is from 50 from 65. In one embodiment, n is selected from 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 56, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 92, 94, 95, 96, 97, 98, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300. In one embodiment, n is 25. In another embodiment n is 57.

The present disclosure also relates to a process of preparing polymers of cyclodextrin conjugates comprising repeating units of cyclodextrin moiety attached through a linker molecule. In the process for preparing polymers of cyclodextrin conjugates, the repeating units of cyclodextrin or its derivative/variant are attached via a linker molecule to afford pbCDK polymer. In an embodiment of the present disclosure, the process of preparing the pbCDK polymer comprises steps of:

1. reacting β-CD with biphenyl-4,4-disulfonylhalide derivative to obtain biphenyl-4,4'-disulfonate capped β-CD;
2. reacting biphenyl-4,4'-disulfonate capped β-CD with sodium azide to obtain diazide derivative of β-CD; and
3. carrying out click reaction (1,3-dipolar cycloaddition reaction) between diazide derivative of β-CD and alkynyloxy-alkane.

In an embodiment of the above process, alkynyloxy-alkane is obtained by reacting a ketone with trialkylsiloxy-1-alkyne in presence of trialkylsilyl triflate and organic solvent.

In another non-limiting embodiment of the aforementioned process, the alkynyloxy-alkane includes but is not limited to dipropergyloxy-propane. In one embodiment, the alkynyloxy-alkane is dipropergyloxy-propane.

In another embodiment of the aforementioned process, the cyclodextrin groups/derivatives/variants are selected from the groups/alternatives provided in the previous embodiments.

The present disclosure particularly provides a process of preparing polymers of cyclodextrin conjugates comprising repeating units of cyclodextrin moiety attached through a triazole-ketal-triazole linker [pbCDK polymer viz. (cyclodextrin-triazole-ketal-triazole)$_n$, wherein n ranges from about 6 to 750]. In the said process, the cyclodextrin units are conjugated via a triazole-ketal-triazole to afford the pbCDK polymer.

In an embodiment of the present disclosure, the process of preparing the pbCDK polymer comprises steps of:
1. reacting β-CD with biphenyl-4,4-disulfonylchloride to obtain biphenyl-4,4'-disulfonate capped β-CD,
2. reacting biphenyl-4,4'-disulfonatecapped β-CD with sodium azide to obtain diazide derivative of β-CD; and
3. carrying out click reaction (1,3-dipolar cycloaddition reaction) between diazide derivative of β-CD and 2,2-dipropergyloxy-propane, to obtain the pbCDK polymer.

In an embodiment of the above process, the aza derivative of β-CD is diazido-β-CD.

In another embodiment of the above process, 2,2-dipropergyloxy-propane is obtained by reacting acetone with 3-trimethylsiloxy-1-propyne in presence of trimethylsilyl trifluoromethanesulphonate and dichloromethane at about −78° C.

In an embodiment of the above processes of preparing polymers of cyclodextrin conjugates, the step-1 is optionally carried out in presence of solvent. In another embodiment, the solvent in step-1 is selected from a group comprising pyridine, N,N'-dimethylformamide, dimethylsulfoxide and a combination thereof.

In an embodiment of the above processes of preparing polymers of cyclodextrin conjugates, the step-2 is optionally carried out in presence of metal halide. In another embodiment, the metal halide in step-2 is selected from a group comprising potassium iodide, sodium iodide and a combination thereof.

In an embodiment of the above processes of preparing polymers of cyclodextrin conjugates, the step-3 is optionally carried out in presence of solvent. In another embodiment, the solvent in step-3 is selected from a group comprising dimethylformamide, dimethyl sulfoxide, tetrahydrofuran, toluene, water, and combinations thereof.

In an embodiment of the above processes, the linker (triazole-ketal-triazole) is formed in the final product (pbCDK polymer) via 1,3-dipolar cycloaddition reaction between alkyne moiety and azide of cyclodextrin.

In an embodiment of the above processes of preparing polymers of cyclodextrin conjugates, 1,3-dipolar cycloaddition reaction between alkyne moiety and azide of cyclodextrin is carried out in presence of a copper salt. In one embodiment, the copper salt is copper tris(triphenylphosphine) bromide, copper iodide, copper bromide and combinations thereof.

In one embodiment, the copper salt is copper tris(triphenylphosphine) bromide.

In still another embodiment of the present disclosure, the above process of synthesizing polymers of cyclodextrin conjugates is carried out at a temperature ranging from about −78° C. to about 100° C. and for a time period ranging from about 1 hour to 48 hours.

Use of Cyclodextrin Polymers for Treating Diseases

In one embodiment of the present disclosure, a method of treating a disease or a condition associated with abnormal NPC1 and/or NPC2 protein production is provided, comprising administering to a subject in need thereof a compound of the present disclosure, e.g., polymers comprising conjugates of cyclodextrins.

The present disclosure further relates to a method for managing or treating lipid storage disorders/lipidoses in a subject having or suspected of having said disorder, comprising administering a therapeutically effective amount of the polymers of cyclodextrin conjugates to the subject. In an embodiment, the present disclosure provides a method for managing or treating lipid storage disorders in a subject having or suspected of having said disorder, the method comprising administering therapeutically effective amount a compound of the present disclosure, including but not limited to, polymers of cyclodextrin conjugates (pbCDK polymer) comprising repeating units of cyclodextrin moiety attached through a triazole-ketal-triazole linker, or a composition/formulation thereof.

In an embodiment of the present disclosure, the lipid storage disorder is a lysosomal lipid storage disorder. In another embodiment, the lysosomal lipid storage disorder is selected from a group comprising sphingolipidoses, wolman disease and a combination thereof. In yet another embodiment, the sphingolipidoses are selected from a group comprising Niemann-Pick type C (NPC), Fabry disease, Krabbe disease, Gaucher disease, Tay-Sachs disease, Metachromatic leukodystrophy, Familial Hypercholesterolemia, Atherosclerosis, multiple sulfatase deficiency and Farber disease, or any combination thereof.

In an exemplary embodiment, the present disclosure relates to a method for managing or treating Niemann-Pick type C (NPC) in a subject having or suspected of having NPC, said method comprising step of administering therapeutically effective amount of pbCDK polymer or a composition/formulation thereof.

The present disclosure also relates to a method of removing lipid from cells of a subject, said method comprising step of administering a therapeutically effective amount of the polymers of cyclodextrin conjugates to the subject. In an embodiment, the lipid includes but is not limited to cholesterol. In an exemplary embodiment, a method of removing cholesterol from cells of a subject is provided, said method comprising step of administering therapeutically effective amount of a compound of the present disclosure, including but not limited to, polymers of cyclodextrin conjugates (pbCDK polymer) comprising repeating units of cyclodextrin moiety attached through triazole-ketal-triazole linker, or a composition/formulation thereof.

In an embodiment of the present disclosure, the subject is a mammal including but not limiting to human.

Without wishing to be bound to any one theory, the inventors hypothesize that the cyclodextrin when released from the polymers of the present invention is capable of complexing with the overexpressed cholesterol or other overexpressed lipids and effluxing it out of the lysosome and thereby significantly lowering the cholesterol content in cells, thereby managing/treating lipid storage disorders. In particular, upon administration of the present pbCDK polymer or a composition/formulation thereof, said polymer accumulates in the different affected organs in the body such as liver, kidney, lungs, spleen and brain. Once in the organs and upon cellular internalization, the polymers enter the cells and degrade to afford free cyclodextrins, followed by the cyclodextrins complexing with the excess cholesterol in the lysosomes and removing them from there. This removal of cholesterol then reduces the diseased state of the cells/organs hence affording the therapeutic effect.

As used in the present disclosure, the expression "management" or "managing" refers to preventing a disease or disorder or condition from occurring in a subject, decreasing the risk of death due to a disease or disorder or condition, delaying the onset of a disease or disorder or condition, inhibiting the progression of a disease or disorder or condition, partial or complete cure of a disease or disorder or condition and/or adverse effect attributable to the said disease or disorder or condition, obtaining a desired pharmacologic and/or physiologic effect (the effect may be prophylactic in terms of completely or partially preventing a disorder or disease or condition, or a symptom thereof and/or may be therapeutic in terms of a partial or complete cure for a disease or disorder or condition and/or adverse effect attributable to the disease or disorder), relieving a disease or disorder or condition (i.e., causing regression of the disease or disorder or condition).

In an embodiment of the above methods, the pbCDK polymer increases the uptake of cyclodextrin in the brain leading to higher neuroprotection efficacy.

In another embodiment of the above methods, the pbCDK polymer crosses blood brain barrier and enter brain cells. This improved penetration of the blood brain barrier can enhance the penetration of a pharmaceutically active agent administered with the present compound.

In yet another embodiment of the above methods, the pbCDK polymer removes overexpressed lipid in brain cells. In an embodiment, the lipid includes but is not limited to cholesterol.

The present invention further relates to the use of polymers of cyclodextrin conjugates or compositions/formulations thereof in management or treatment of lipid storage disorders. In one embodiment, use of pbCDK polymer or compositions/formulations comprising the same for management of lipid storage disorders is provided.

In an embodiment, the lipid storage disorder is lysosomal lipid storage disorder. In another embodiment, the lysosomal lipid storage disorder is selected from a group comprising sphingolipidoses, wolman disease and a combination thereof. In yet another embodiment, the sphingolipidoses are selected from a group comprising Niemann-Pick type C (NPC), Fabry disease, Krabbe disease, Gaucher disease, Tay-Sachs disease, Metachromatic leukodystrophy, Familial Hypercholesterolemia, Atherosclerosis, multiple sulfatase deficiency, Farber disease, renal disorders that are a cholesterol homeostasis such as Focal Segmental Glomerulosclerosis, Alport Syndrome, Diabetic Kidney, and combinations thereof.

In an exemplary embodiment, the present disclosure provides pbCDK polymer or compositions/formulations thereof for use in managing or treating NPC.

The present disclosure also provides a pharmaceutical composition or formulation comprising therapeutically effective amount of a polymer as described herein, optionally along with excipient(s).

In an embodiment of the present disclosure, the excipient is selected from a group comprising, but not limited to, granulating agent, binding agent, lubricating agent, disintegrating agent, sweetening agent, glidant, anti-adherent, antistatic agent, surfactant, anti-oxidant, gum, coating agent, coloring agent, flavouring agent, coating agent, plasticizer, preservative, suspending agent, emulsifying agent, plant cellulosic material, spheronization agents and combinations thereof.

In another embodiment, the pharmaceutical composition disclosed herein further comprises a therapeutically active agent. In some embodiments, a therapeutically active agent includes those useful in treatment of lipid storage disorders. In some embodiments, a therapeutically active agent includes paclitaxel, camptothecin, voriconazole, cyclosporine A, doxorubicin, and combinations thereof.

In a further embodiment of the present disclosure, a pharmaceutical composition comprising one or more polymers of the present disclosure, e.g., polymers comprising conjugates of cyclodextrins, and a pharmaceutically acceptable excipient or adjuvant is provided. The pharmaceutically acceptable excipients and adjuvants are added to the composition or formulation for a variety of purposes. In another embodiment, a pharmaceutical composition comprising one or more polymers of the present disclosure, e.g., polymers comprising conjugates of cyclodextrins, further comprises a pharmaceutically acceptable carrier. In one embodiment, a pharmaceutically acceptable carrier includes a pharmaceutically acceptable excipient, binder, and/or diluent. In one embodiment, suitable pharmaceutically acceptable excipients include, but are not limited to, water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, the pharmaceutical compositions of the present disclosure may additionally contain other adjunct components conventionally found in pharmaceutical compositions, at their art-established usage levels. Thus, for example, the pharmaceutical compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions described herein. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

Cyclodextrin Polymer Dosage and Administration

In particular, a pharmaceutical composition or formulation comprising about 4 mg/kg body weight (b.w.) to 4000 mg/kg b.w. of the patient of pbCDK polymer, optionally along with excipient(s) is provided.

In an embodiment, a pharmaceutical composition or formulation comprising about 4 mg/kg b.w. to 120 mg/kg b.w. of the patient of pbCDK polymer, optionally along with excipient(s) is provided.

In another embodiment, a pharmaceutical composition or formulation comprising 4 mg/kg b.w. to 400 mg/kg b.w. of the patient of pbCDK polymer, optionally along with excipient(s) is provided.

In yet another embodiment, a pharmaceutical composition or formulation comprising 100 mg/kg b.w. to 1000 mg/kg b.w. of the patient of pbCDK polymer, optionally along with excipient(s) is provided.

In still another embodiment, a pharmaceutical composition or formulation comprising 200 mg/kg b.w. to 2000 mg/kg b.w. of the patient of pbCDK polymer, optionally along with excipient(s) is provided.

In still another embodiment, a pharmaceutical composition or formulation comprising 300 mg/kg b.w. to 3000 mg/kg b.w. of the patient of pbCDK polymer, optionally along with excipient(s) is provided.

In certain embodiments, the pharmaceutical formulation comprises the present polymer in an amount of from about 1 mg/kg b.w. to about 10 g/kg b.w. In some embodiments, the pharmaceutical formulation comprises the present polymer in an amount of about 2 mg/kg b.w. In some embodiments, the pharmaceutical formulation comprises the present polymer in an amount of about 3 mg/kg b.w. In some embodiments, the pharmaceutical formulation comprises the present polymer in an amount of about 4 mg/kg b.w. In some embodiments, the pharmaceutical formulation comprises the present polymer in an amount of about 5 mg/kg b.w. In some embodiments, the pharmaceutical formulation comprises the present polymer in an amount of about 6 mg/kg b.w. In some embodiments, the pharmaceutical formulation comprises the present polymer in an amount of about 7 mg/kg b.w. In some embodiments, the pharmaceutical formulation comprises the present polymer in an amount of about 8 mg/kg b.w. In some embodiments, the pharmaceutical formulation comprises the present polymer in an amount of about 9 mg/kg b.w. In some embodiments, the pharmaceutical formulation comprises the present polymer in an amount of about 10 mg/kg b.w. In some embodiments, the pharmaceutical formulation comprises the present polymer in an amount of about 20 mg/kg b.w. In some embodiments, the pharmaceutical formulation comprises the present polymer in an amount of about 30 mg/kg b.w. In some embodiments, the pharmaceutical formulation comprises the present polymer in an amount of about 40 mg/kg b.w. In some embodiments, the pharmaceutical formulation comprises the present polymer in an amount of about 50 mg/kg b.w. In some embodiments, the pharmaceutical formulation comprises the present polymer in an amount of about 60 mg/kg b.w. In some embodiments, the pharmaceutical formulation comprises the present polymer in an amount of about 70 mg/kg b.w. In some embodiments, the pharmaceutical formulation comprises the present polymer in an amount of about 80 mg/kg b.w. In some embodiments, the pharmaceutical formulation comprises the present polymer in an amount of about 90 mg/kg b.w. In some embodiments, the pharmaceutical formulation comprises the present polymer in an amount of about 100 mg/kg b.w. In some embodiments, the pharmaceutical formulation comprises the present polymer in an amount of about 200 mg/kg b.w. In some embodiments, the pharmaceutical formulation comprises the present polymer in an amount of about 300 mg/kg b.w. In some embodiments, the pharmaceutical formulation comprises the present polymer in an amount of about 400 mg/kg b.w. In some embodiments, the pharmaceutical formulation comprises the present polymer in an amount of about 500 mg/kg b.w. In some embodiments, the pharmaceutical formulation comprises the present polymer in an amount of about 600 mg/kg b.w. In some embodiments, the pharmaceutical formulation comprises the present polymer in an amount of about 700 mg/kg b.w. In some embodiments, the pharmaceutical formulation comprises the present polymer in an amount of about 800 mg/kg b.w. In some embodiments, the pharmaceutical formulation comprises the present polymer in an amount of about 900 mg/kg b.w. In some embodiments, the pharmaceutical formulation comprises the present polymer in an amount of about 1000 mg/kg b.w. In some embodiments, the pharmaceutical formulation comprises the present polymer in an amount of about 2000 mg/kg b.w. In some embodiments, the pharmaceutical formulation comprises the present polymer in an amount of about 3000 mg/kg b.w.

In an embodiment of the present disclosure, the patient is a mammal including but not limited to a human.

In another aspect of the present disclosure, the polymer of the present disclosure or the pharmaceutical composition/formulation comprising the same is administered by mode selected from a group comprising intravenous, subcutaneous, transdermal, intrathecal, intranasal, intracisternal, oral and any other compatible mode and combinations thereof.

In one embodiment, the pbCDK polymer of the present disclosure or the pharmaceutical composition/formulation comprising the same is administered subcutaneously, intranasally or a combination thereof.

In an exemplary embodiment, the pbCDK polymer of the present disclosure or the pharmaceutical composition/formulation comprising the same is administered subcutaneously.

In another exemplary embodiment, the pbCDK polymer of the present disclosure or the pharmaceutical composition/formulation comprising the same is administered intranasally.

In yet another exemplary embodiment, the pbCDK polymer of the present disclosure or the pharmaceutical composition/formulation comprising the same is administered by a combination of subcutaneous and intranasal administration.

The polymers disclosed herein can be formulated in accordance with the routine procedures adapted for desired administration route. Accordingly, the polymers disclosed herein can take such forms as suspensions, solutions or emulsions in oily or aqueous vehicles, and can contain formulatory agents such as suspending, stabilizing and/or dispersing agents. The polymers disclosed herein can also be formulated as a preparation for implantation or injection. Thus, for example, the polymers can be formulated with suitable polymeric or hydrophobic materials (e.g., as an emulsion in an acceptable oil) or ion exchange resins, or as sparingly soluble derivatives (e.g., as a sparingly soluble salt). Alternatively, the active ingredient can be in powder form for constitution with a suitable vehicle, e.g., sterile pyrogen-free water, before use. Suitable formulations for each of these methods of administration can be found, for example, in Remington: The Science and Practice of Pharmacy, A. Gennaro, ed., 20th edition, Lippincott, Williams & Wilkins, Philadelphia, Pa.

In another embodiment of the present disclosure, the pharmaceutical composition/formulation is formulated into forms selected from a group comprising, but not limited to, solution, aqueous suspension, capsule, tablet, injection, cream, gel, ointment, lotion, emulsion, foam, troche, lozenge, oily suspension, patch, dentifrice, spray, drops, dispersible powder or granule, syrup, elixir, food stuff, and any combination of forms thereof.

The polymer technology approach of the present disclosure provides increased retention time of cyclodextrin in the body thereby improving the pharmacokinetic and biodistribution profile and hence enabling prolonged therapeutic action. This can be attributed to the reduced rate of renal clearance due to its large size. Consequently, the doses required to maintain therapeutic concentrations are significantly reduced in view of the prolonged circulation time in the body. This in turn allows less frequent administration which increases patient compliance significantly.

The present disclosure also provides a method of increasing the uptake of cyclodextrin in the brain of a subject, said method comprising administering said cyclodextrin as polymer of cyclodextrin conjugates to the subject. In particular, the present disclosure provides a method of increasing the uptake of cyclodextrin in the brain of a subject, said method comprising a step of administering a therapeutically effective amount of pbCDK polymer or a composition/formulation thereof to said subject.

The present disclosure further provides a method of delivering cyclodextrin to brain cells of a subject, said method comprising a step of administering a therapeutically effective amount of polymer of cyclodextrin conjugates to said subject. In particular, the present disclosure provides a method of delivering cyclodextrin to brain cells of a subject, said method comprising step of administering a therapeutically effective amount of pbCDK polymer or a composition/formulation thereof to said subject.

In an embodiment of the above methods, the subject is a mammal including but not limiting to human.

Formulation and Manufacturing

In certain embodiments, a pharmaceutical composition of the present disclosure is prepared using known techniques, including, but not limited to mixing, dissolving, granulating, dragee-making, levigating, emulsifying, encapsulating, entrapping or tableting processes.

In one embodiment, the present disclosure provides a pharmaceutical composition comprising a polymer of the present disclosure, e.g., polymers comprising conjugates of cyclodextrins, as disclosed herein, combined with a pharmaceutically acceptable carrier. In one embodiment, suitable pharmaceutically acceptable carriers include, but are not limited to, inert solid fillers or diluents and sterile aqueous or organic solutions. Pharmaceutically acceptable carriers are well known to those skilled in the art and include, but are not limited to, from about 0.01 to about 0.1 M and preferably 0.05M phosphate buffer or 0.8% saline. Such pharmaceutically acceptable carriers can be aqueous or non-aqueous solutions, suspensions and emulsions. Examples of non-aqueous solvents suitable for use in the present application include, but are not limited to, propylene glycol, polyethylene glycol, vegetable oils such as olive oil, and injectable organic esters such as ethyl oleate.

Aqueous carriers suitable for use in the present application include, but are not limited to, water, ethanol, alcoholic/aqueous solutions, glycerol, emulsions or suspensions, including saline and buffered media. Oral carriers can be elixirs, syrups, capsules, tablets and the like.

Liquid carriers suitable for use in the present application can be used in preparing solutions, suspensions, emulsions, syrups, elixirs and pressurized polymers. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid carriers suitable for use in the present application include, but are not limited to, water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also include an oily ester such as ethyl oleate and isopropyl myristate. Sterile liquid carriers are useful in sterile liquid form comprising polymers for parenteral administration. The liquid carrier for pressurized polymers disclosed herein can be halogenated hydrocarbon or other pharmaceutically acceptable propellant.

Solid carriers suitable for use in the present application include, but are not limited to, inert substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets preferably contain up to 99% of the active compound. Suitable solid carriers include, for example, calcium phosphate, magnesium stearate, talc, sugars, lactose, dextrin, starch, gelatin, cellulose, polyvinylpyrrolidine, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxy methyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

Parenteral carriers suitable for use in the present application include, but are not limited to, sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like.

Carriers suitable for use in the present application can be mixed as needed with disintegrants, diluents, granulating agents, lubricants, binders and the like using conventional techniques known in the art. The carriers can also be sterilized using methods that do not deleteriously react with the polymers, as is generally known in the art.

Diluents may be added to the formulations of the present invention. Diluents increase the bulk of a solid pharmaceutical composition and/or combination, and may make a pharmaceutical dosage form containing the composition and/or combination easier for the patient and care giver to handle. Diluents for solid compositions and/or combinations include, for example, microcrystalline cellulose (e.g., AVICEL), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, and talc.

Additional embodiments relate to the pharmaceutical formulations wherein the formulation is selected from the group consisting of a solid, powder, liquid and a gel. In certain embodiments, a pharmaceutical composition of the present invention is a solid (e.g., a powder, tablet, a capsule, granulates, and/or aggregates). In certain of such embodiments, a solid pharmaceutical composition comprising one or more ingredients known in the art, including, but not limited to, starches, sugars, diluents, granulating agents, lubricants, binders, and disintegrating agents.

Solid pharmaceutical compositions that are compacted into a dosage form, such as a tablet, may include excipients whose functions include helping to bind the active ingredient and other excipients together after compression. Binders for solid pharmaceutical compositions and/or combinations include acacia, alginic acid, carbomer (e.g., carbopol), carboxymethylcellulose sodium, dextrin, ethyl cellulose, gelatin, guar gum, gum tragacanth, hydrogenated vegetable oil, hydroxyethyl cellulose, hydroxypropyl cellulose (e.g., KLUCEL), hydroxypropyl methyl cellulose (e.g., METHOCEL), liquid glucose, magnesium aluminum silicate, maltodextrin, methylcellulose, polymethacrylates, povidone (e.g., KOLLIDON, PLASDONE), pregelatinized starch, sodium alginate, and starch.

The dissolution rate of a compacted solid pharmaceutical composition in the patient's stomach may be increased by the addition of a disintegrant to the composition and/or combination. Disintegrants include alginic acid, carboxymethylcellulose calcium, carboxymethylcellulose sodium (e.g., AC-DI-SOL and PRIMELLOSE), colloidal silicon dioxide, croscarmellose sodium, crospovidone (e.g., KOLLIDON and POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB), potato starch, and starch.

Glidants can be added to improve the flowability of a non-compacted solid composition and/or combination and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition and/or combination to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition and/or combination of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

Liquid pharmaceutical compositions can be prepared using polymers of the present disclosure, e.g., polymers comprising conjugates of cyclodextrins, and any other solid excipients where the components are dissolved or suspended in a liquid carrier such as water, vegetable oil, alcohol, polyethylene glycol, propylene glycol, or glycerin.

For example, formulations for parenteral administration can contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxy ethylene-polyoxypropylene copolymers can be useful excipients to control the release of active compounds. Other potentially useful parenteral delivery systems include ethylene-vinyl acetate copolymer particles, osmotic pumps, implantable infusion systems, and liposomes. Formulations for inhalation administration contain as excipients, for example, lactose, or can be aqueous solutions containing, for example, polyoxyethylene-9-auryl ether, glycocholate and deoxycholate, or oily solutions for administration in the form of nasal drops, or as a gel to be applied intranasally. Formulations for parenteral administration can also include glycocholate for buccal administration, methoxysalicylate for rectal administration, or citric acid for vaginal administration.

Liquid pharmaceutical compositions can contain emulsifying agents to disperse uniformly throughout the composition and/or combination an active ingredient or other excipient that is not soluble in the liquid carrier. Emulsifying agents that may be useful in liquid compositions and/or combinations of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as aspartame, lactose, sorbitol, saccharin, sodium saccharin, sucrose, aspartame, fructose, mannitol, and invert sugar may be added to improve the taste.

Preservatives and chelating agents such as alcohol, sodium benzoate, butylated hydroxyl toluene, butylated hydroxyanisole, and ethylenediamine tetraacetic acid may be added at levels safe for ingestion to improve storage stability.

A liquid composition can also contain a buffer such as gluconic acid, lactic acid, citric acid or acetic acid, sodium gluconate, sodium lactate, sodium citrate, or sodium acetate. Selection of excipients and the amounts used may be readily determined by the formulation scientist based upon experience and consideration of standard procedures and reference works in the field.

In one embodiment, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Formulations for intravenous administration can comprise solutions in sterile isotonic aqueous buffer. Where necessary, the formulations can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the polymer is to be administered by infusion, it can be dispensed in a formulation with an infusion bottle containing sterile pharmaceutical grade water, saline or dextrose/water. Where the polymer is administered by injection, an ampule of sterile water for injection or saline can be provided so that the ingredients can be mixed prior to administration.

Suitable formulations further include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

In certain embodiments, a pharmaceutical composition of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80 and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

Appropriate pharmaceutical compositions of the present disclosure can be determined according to any clinically-acceptable route of administration of the composition to the subject. The manner in which the composition is administered is dependent, in part, upon the cause and/or location. One skilled in the art will recognize the advantages of certain routes of administration. The method includes administering an effective amount of the agent or compound (or composition comprising the agent or compound) to achieve a desired biological response, e.g., an amount effective to alleviate, ameliorate, or prevent, in whole or in part, a symptom of a condition to be treated, e.g., oncology and neurology disorders. In various aspects, the route of administration is systemic, e.g., oral or by injection. The agents or polymer, or pharmaceutically acceptable salts or derivatives thereof, are administered orally, nasally, transdermally, pulmonary, inhalationally, buccally, sublingually, intraperintoneally, subcutaneously, intramuscularly, intravenously, rectally, intrapleurally, intrathecally, intraportally, and parenterally. Alternatively or in addition, the route of administration is local, e.g., topical, intra-tumor and pen-tumor. In some embodiments, the polymer is administered orally.

In certain embodiments, a pharmaceutical composition of the present disclosure is prepared for oral administration. In certain of such embodiments, a pharmaceutical composition is formulated by combining one or more agents and pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In other embodiments the polymer of the present disclosure are administered by the intravenous route. In further embodiments, the parenteral administration may be provided in a bolus or by infusion.

In certain embodiments, a pharmaceutical composition is prepared for rectal administration, such as a suppository or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

The concentration of a disclosed polymer in a pharmaceutically acceptable mixture will vary depending on several factors, including the dosage of the polymer to be administered, the pharmacokinetic characteristics of the polymer(s) employed, and the route of administration. The agent may be administered in a single dose or in repeat doses. The dosage regimen utilizing the polymers of the present invention is selected in accordance with a variety of factors including type, species, age, weight, sex and medical condition of the patient; the severity of the condition to be treated; the route of administration; the renal and hepatic function of the patient; and the particular polymer employed. Treatments may be administered daily or more frequently depending upon a number of factors, including the overall health of a patient, and the formulation and route of administration of the selected compound(s). An ordinarily skilled physician or veterinarian can readily determine and prescribe the effective amount of the polymer required to prevent, counter or arrest the progress of the condition.

The polymers or pharmaceutical compositions of the present disclosure may be manufactured and/or administered in single or multiple unit dose forms.

Having now generally described the invention, the same will be more readily understood through reference to the following examples, which are provided by way of illustration and are not intended to be limiting of the present invention.

Additional embodiments and features of the present disclosure will be apparent to one of ordinary skill in art based upon description provided herein. The embodiments herein and the various features and advantageous details thereof are explained with reference to the non-limiting embodiments in the description. Descriptions of well-known/conventional methods and techniques are omitted so as to not unnecessarily obscure the embodiments herein. The examples presented herein are intended merely to facilitate an understanding of ways in which the embodiments herein may be practiced and to further enable those of skill in the art to practice the embodiments herein. Accordingly, the following examples should not be construed as limiting the scope of the present disclosure.

EXAMPLES
Example 1
Procedure for Synthesis of pbCDK Polymer
Step 1: Synthesis of biphenyl-4,4'-disulfonatecapped β-CD (1)
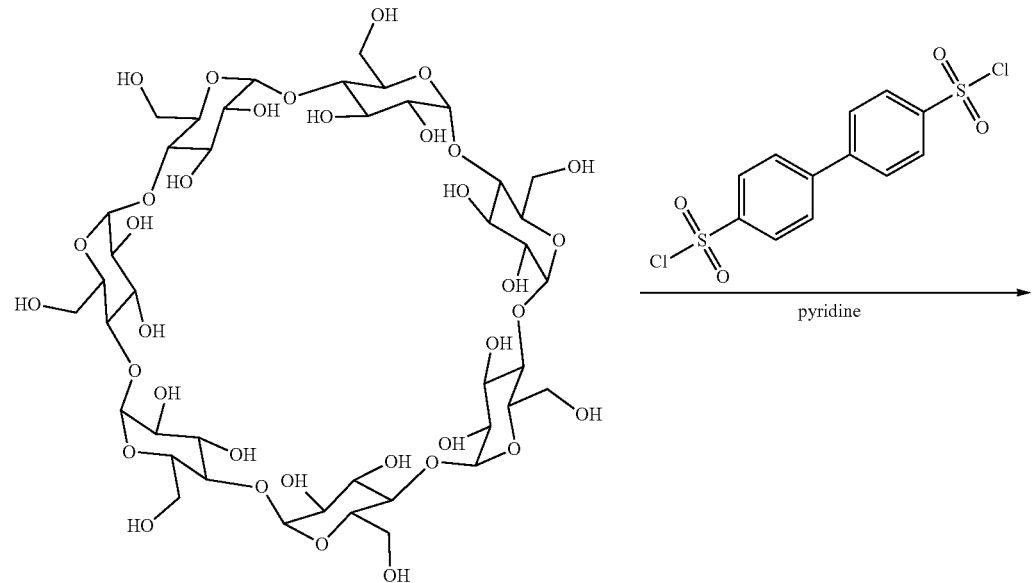
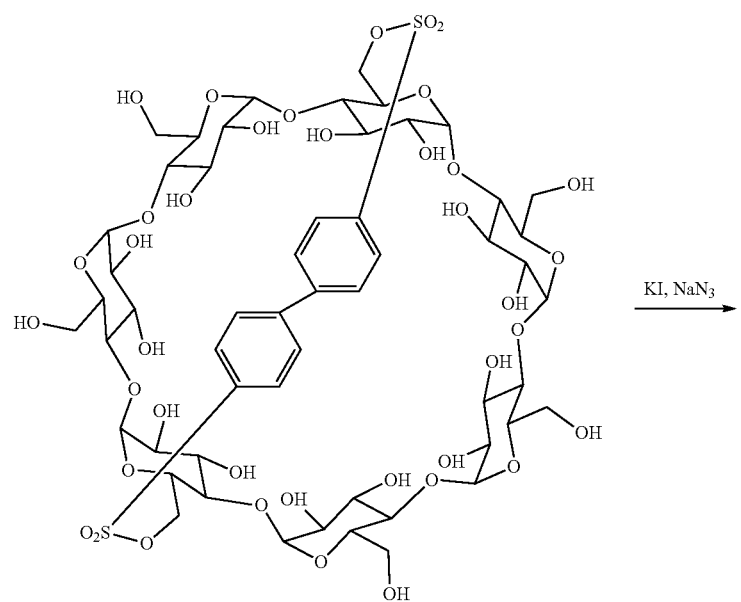

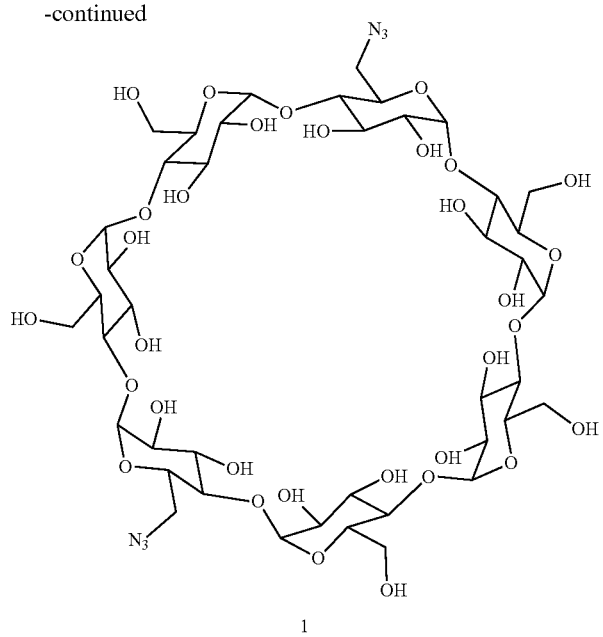

1

To a solution of β-CD (about 10 g, 8.81 mmol) in about 250 ml of freshly distilled anhydrous pyridine, about 2.78 g (7.93 mmol) of biphenyl-4,4-disulfonylchloride is added in four equal portions at about 15 minute intervals. The resulting solution is stirred at about 60° C. under nitrogen atmosphere for an additional 3 hours and the solvent was removed to dryness in vacuum at room temperature. The residue was subjected to column chromatography using gradient elution of 10-20% water in acetonitrile. Fractions were analyzed by HPLC and the appropriate fractions were combined. After removing acetonitrile on a rotary evaporator, the resulting aqueous suspension was lyophilized to dryness. This procedure gave about 5.42 g (40% yield) of βCD-(OTs)$_2$ (Compound 1). $^1$H NMR (300 MHz, H$_2$O) δ: 3.58-3.65 (t, 19H), 5-5.3 (q, 7H), 3.9-4.3 (t, 7H), 3-3.2 (d, 7H), 3.5-3.7 (t, 14H), 7.6-8.1 (d, 8H).

Step 2: Synthesis of Diazido-β-CD (1)

To a solution of about 10 g (1 mmol) of βCD-(OTs)$_2$ in about 200 ml of dry DMF, about 11.7 g (10 mmol) of dry powdered potassium iodide is added. The solution is kept at about 80° C. for about 2 hours with stirring. After about 2 hours of heating, about 10 g of sodium azide (10 mmol) is added and stirred at about 80° C. for about another 12 hours. The solvent is removed on rotary evaporator under reduced pressure and residue is dissolved in about 100 ml of water. The reaction mixture is filtered to remove excess salt. The resulting aqueous suspension is lyophilized to dryness. The residue is subjected to column chromatography using gradient elution of 10-20% water in acetonitrile. Mass spec. (m/z=1184.3).

Step 3: Synthesis of 2,2-Dipropergyloxy-Propane (2)

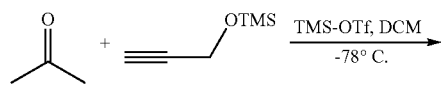

-continued

2

A flame dried two-neck round bottom flask is equipped with stirred bar and cooled down under an argon stream. Dry DCM (about 3 mL), 3-trimethylsiloxy-1-propyne (about 4.4 g, 0.034 mol) and acetone (about 1.2 mL, 0.017 mol) are added under inert atmosphere at room temperature. The reaction mixture was cooled down to about −78° C. and trimethylsilyl trifluoromethanesulphonate (about 50 μL, 20 mol %) was added to the reaction mixture. The solution is stirred at about −78° C. for about 2.5 hours. After completion of the reaction pyridine (about 0.6 mL) is added. The reaction mixture is poured in to saturated NaHCO$_3$ (about 20 mL) and extracted with ether (about 70 mL). The collective organic layer is washed with brine (2×25 mL). The crude product is purified (hexane/triethyl amine=100/1) by silica gel column chromatography to afford Compound 2 (about 1.5 g, 58%) as a colourless oil. $^1$H NMR (400 MHz, CDCl$_3$) δ: 4.14 (d, 4H, J=2 Hz), 2.39 (t, 2H, J=2 Hz), 1.41 (s, 6H). $^{13}$C NMR (150 MHz, CDCl3) d: 101.59 (s), 80.45 (s), 73.42 (s), 49.44 (s), 24.67 (s). HRMS (70 eV, EI): calcd for C9H13O2 [M]+: calcd 152.0837, found 152.084.

Step 4: Click Reaction to Synthesize pbCDK Polymer

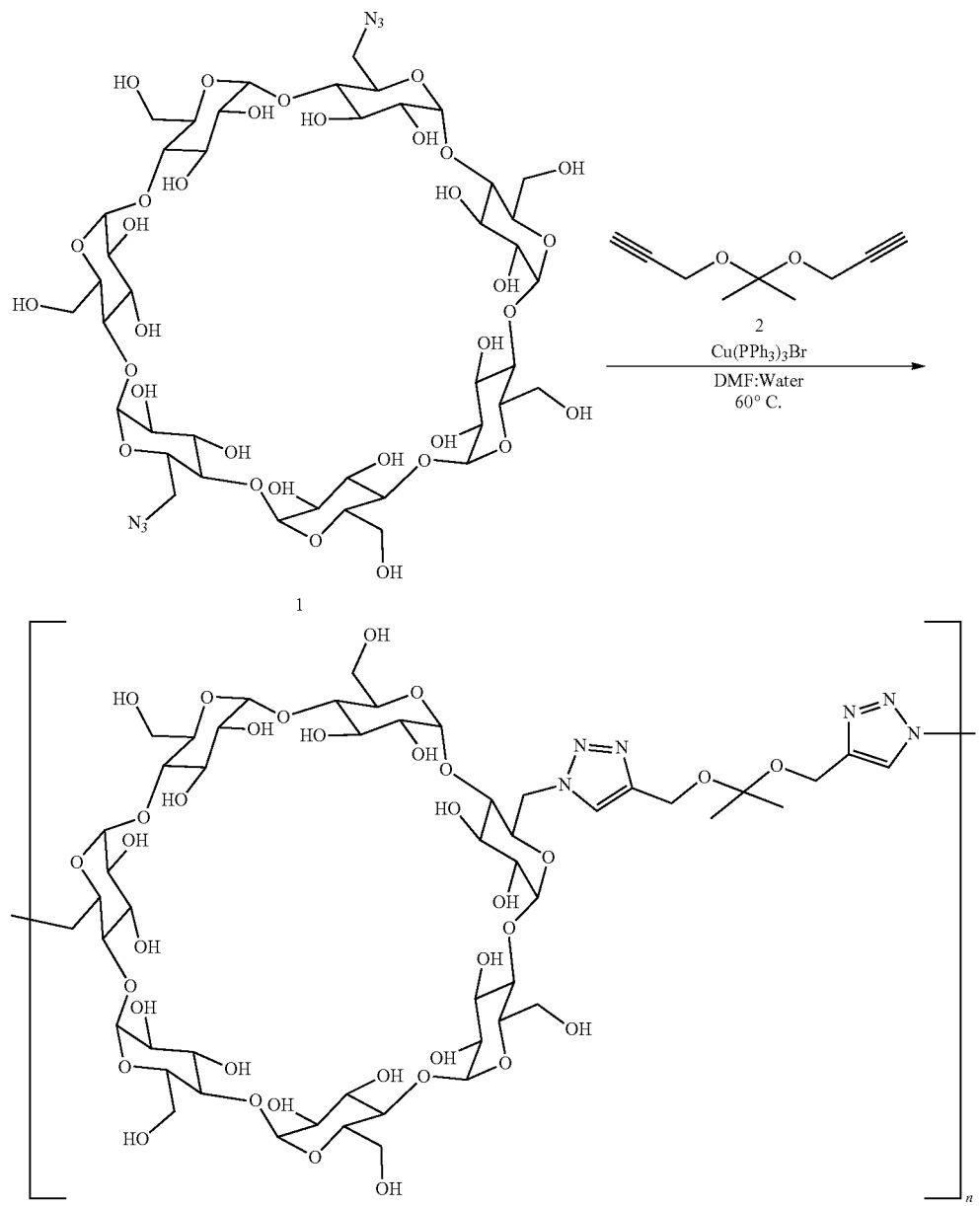

wherein n ranges from 6 to 750.

General Procedure: To a degassed solution of 1 in solvent (DMF or DMF:Water 1:1 or THF:Water 1:1), 2 and Cu(PPh$_3$)$_3$Br (5 mol %) is added. The solution is stirred with heating at 55° C.-60° C. for about 24 hours. The viscous solution is poured into a large excess of ethyl acetate (hexane or acetone or diethyl ether) (10× of reaction volume). The resulting precipitate is removed by centrifugation. The solid product is re-dissolved and re-precipitated in (acetone, hexane, or ethyl acetate) respectively. The same process is continued for about 3 times to achieve an off white powder i.e., pbCDK polymer. The molecular weight of the pbCDK polymer is determined with gel permeation chromatography (GPC) in DMF.

Polymer A—n is approximately 25

Figure 4:
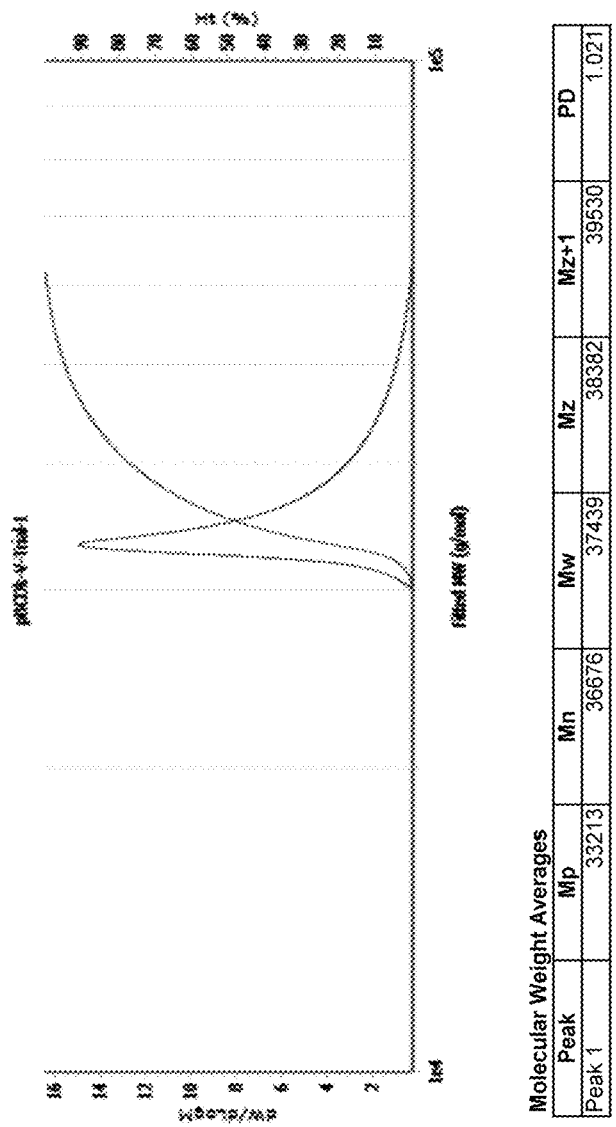
FIG. 4 shows a gel permeation chromatograph of Polymer A.
Figure 5:
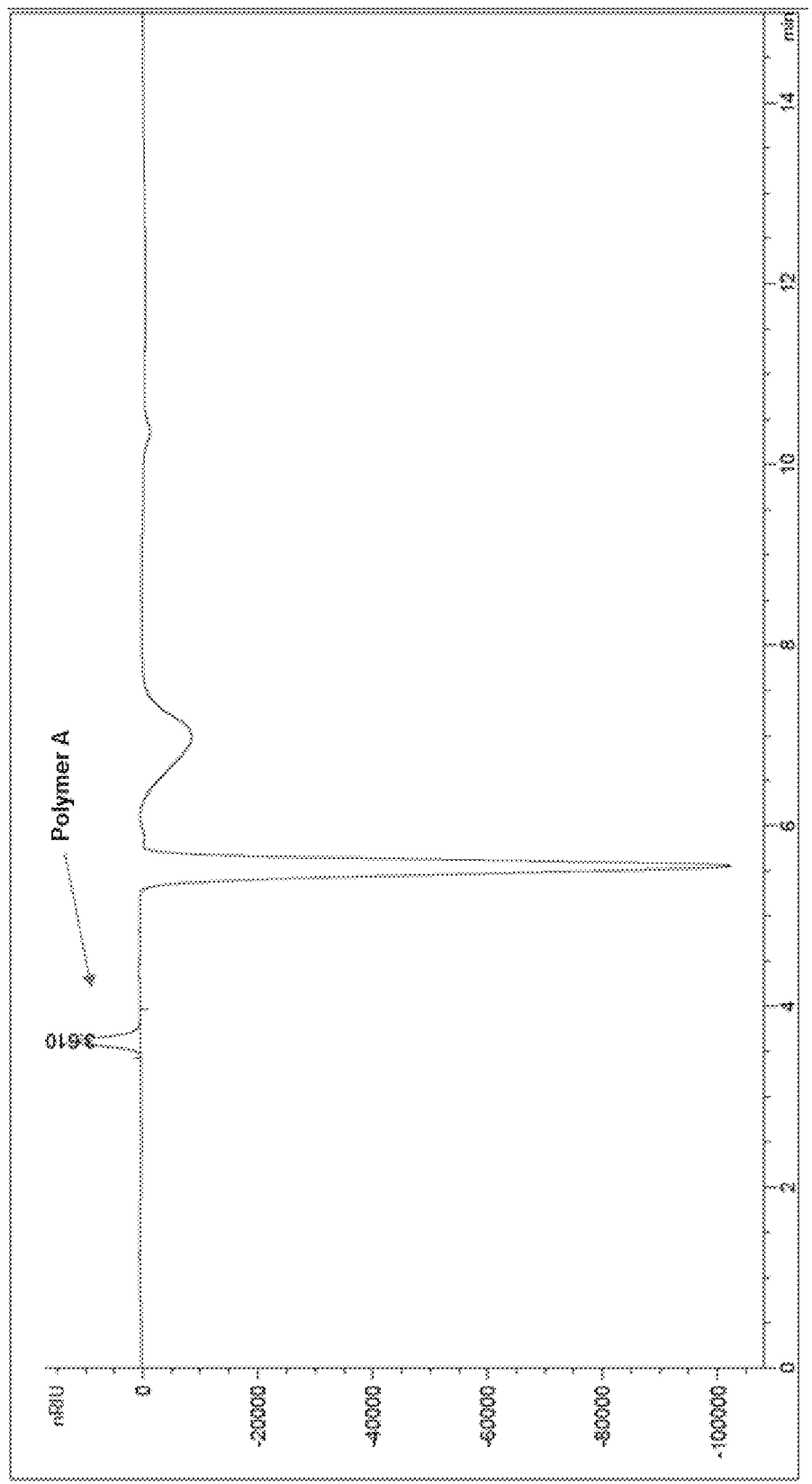
FIG. 5 shows an HPLC analysis of Polymer A.

Polymer A was synthesized according to the General Procedure discussed above, employing 1 g of 1 and 128 mg of 2 stirred at 55° C. for 24 h. Polymer A has a molecular weight peak (Mp) of 33,213 g/mol and a polydispersity index (PDI) of 1.021. Polymer A was characterized with GPC (FIG. 4) and HPLC (FIG. 5).

Polymer B—n is approximately 57

Figure 6:
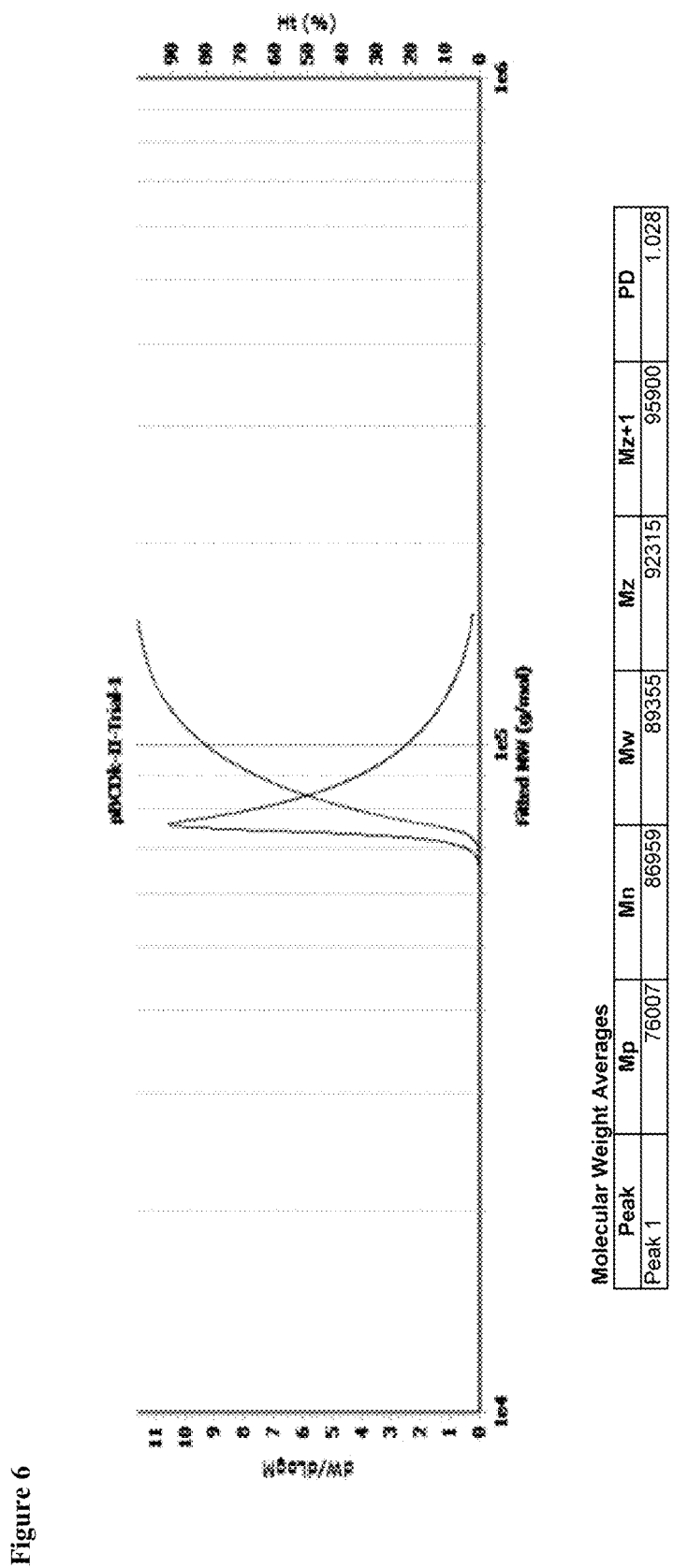
FIG. 6 shows a gel permeation chromatograph of Polymer B.
Figure 7:
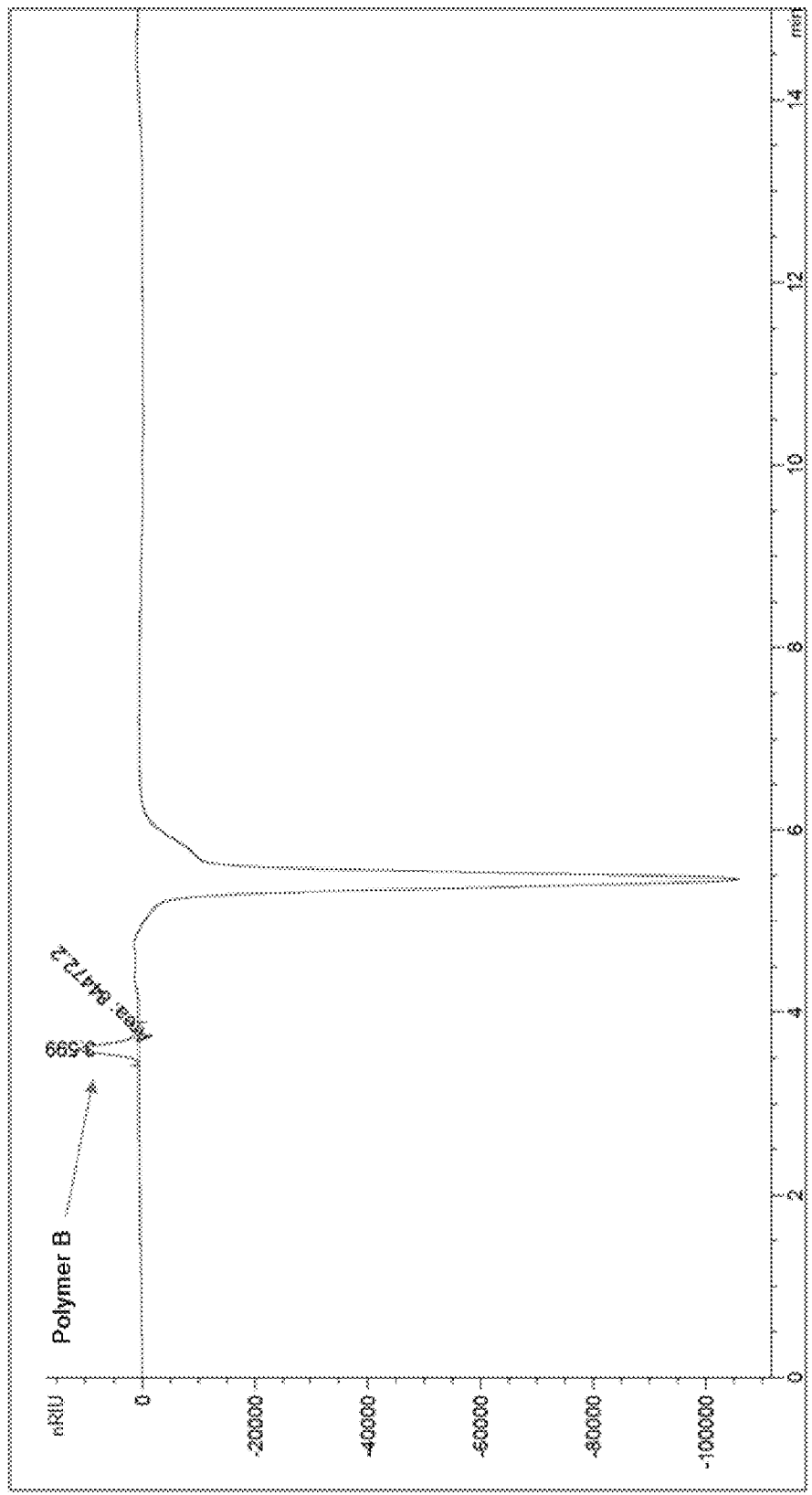
FIG. 7 shows an HPLC analysis of Polymer B.

Polymer B was synthesized according to the General Procedure discussed above, employing 1 g of 1 and 128 mg of 2 stirred at 55° C. for 24 h. Polymer B has a molecular weight peak (Mp) of 76,007 g/mol and a polydispersity index (PDI) of 1.028. Polymer B was characterized with GPC (FIG. 6) and HPLC (FIG. 7).

Example 2

In Vitro Cellular Uptake Study

Figure 8:
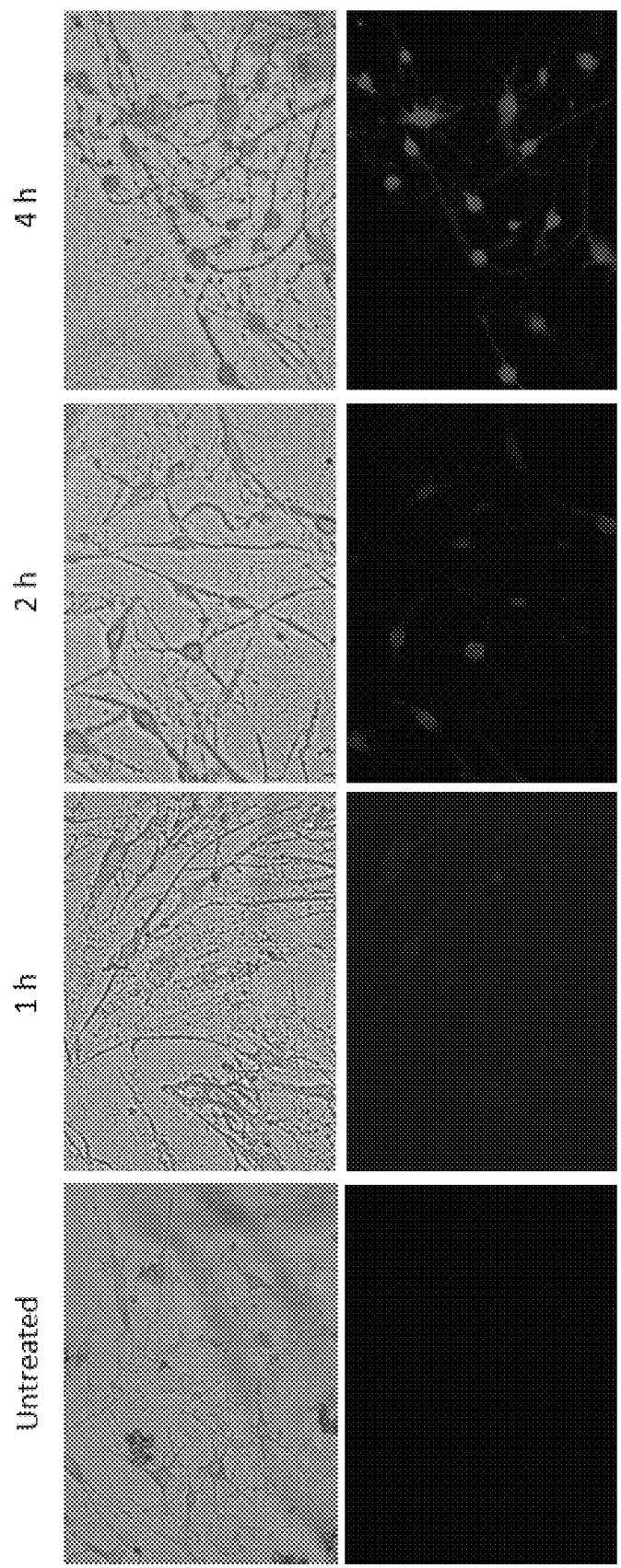
FIG. 8 shows in vitro cellular uptake of Polymer A in $NPC^{-/-}$ fibroblast cells.

Polymer A was labelled with Tetramethylrhodamine (TRITC) dye to obtain Polymer A-TRITC. NPC patient derived fibroblasts were seeded in 8 well chamber slides at a density of 6000 cells/well. 50 µM of Polymer A-TRITC was added to the wells and the cells were allowed to incubate for 4 h. At the end of the 4 h incubation, the spent media was removed and the cells were washed with PBS thrice to remove any unbound polymer. Imaging was performed using the Floid Cell Imaging System. (FIG. 8).

Example 3

Subcutaneous Administration of Polymer A in Mice

Figure 9:
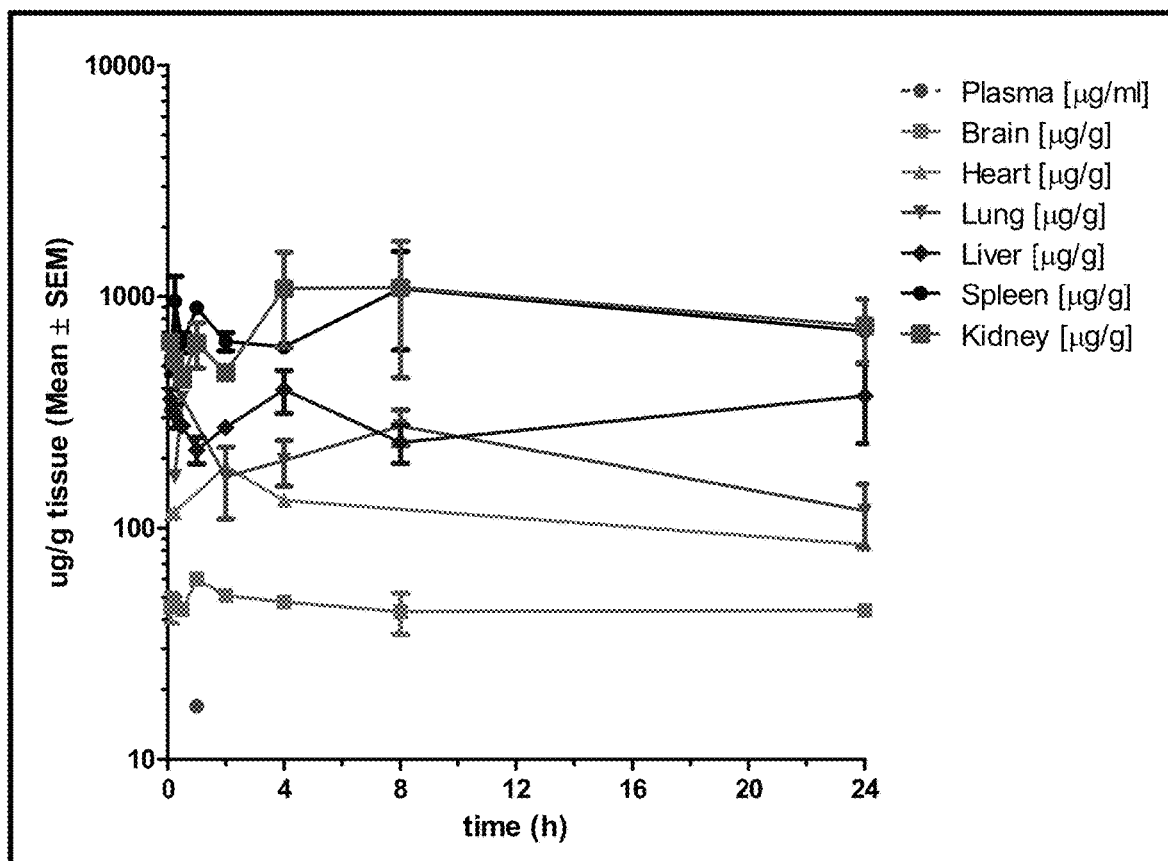
FIG. 9 shows biodistribution profile of Polymer A in mice after subcutaneous administration.

An HPLC-UV based bioanalytical method was developed in mouse plasma for Polymer A. The method was linear between 13.4 and 500 µg/ml plasma, with an LLOQ of 13.4 µg/ml, was precise and accurate. The recovery was >90% from plasma and tissues. The PK and tissue distribution of pBCDK was performed in mice following a single subcutaneous dose of 100 mg/kg. The concentration of Polymer A in various cells were monitored over 24 h. Uptake and retention of Polymer A in organs including brain, lungs, liver, spleen, and kidney were observed (FIG. 9). Error bars in FIG. 9 are SEM.

Example 4

Blood Brain Barrier Uptake of Subcutaneous Administration of Polymer A in Mice Polymer A-TRITC was dissolved at 5% w/v solution in sterile filtered water. A single subcutaneous dose of this solution was administered to PN14 mice 6 h before sacrifice. Upon sacrifice tissue sections of the cerebellum and olfactory bulb were observed under a fluorescence microscope in the TRITC channel. Blood brain barrier uptake was observed for Polymer A-TRITC after subcutaneous administration.

Example 5

Efficacy Study in Npc1$^{nih}$ Mouse Models (Polymer B)

Npc1$^{nih}$ mouse model is a model for an early onset and faster progressing human diseases. This mouse model arises from the insertion of an active retrotransposon, a spontaneous mutation, which generated a frameshift resulting in a "knock out" of Npc1 gene: small amount of truncated Npc1 mRNA and no protein.

Npc1$^{nih}$ mice received Polymer B (0.8 mg/g body weight) via injection (s.c.) at the scruff of the neck at PN4, PN7, and PN14. Another group of Npc1$^{nih}$ mice received HPβCD (4 mg/g body weight; obtained from Sigma-Aldrich and used as received, CAS: 128446-35-5) via injected (s.c.) weekly starting at PN7. Control mice received PBS (sham). Mean volume of the injection was between 50 to 100 µL according to mice size. The body weight, motor behaviour, and survival rate of each group of mice were analyzed.

Figure 10A:
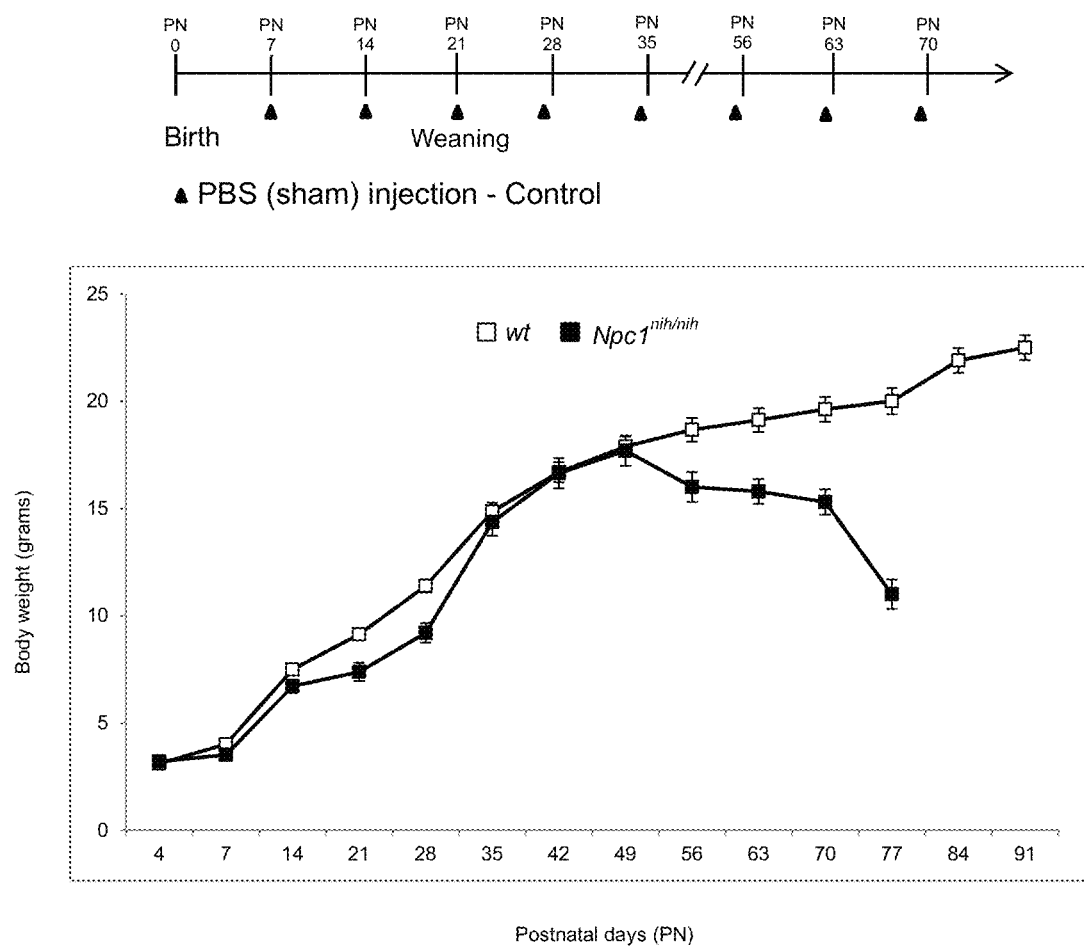
FIG. 10A shows the dosing regimen of control WT and PBS sham $Npc1^{nih}$ groups in the efficacy studies. Body weight of the control groups during the study is shown.
Figure 10B:
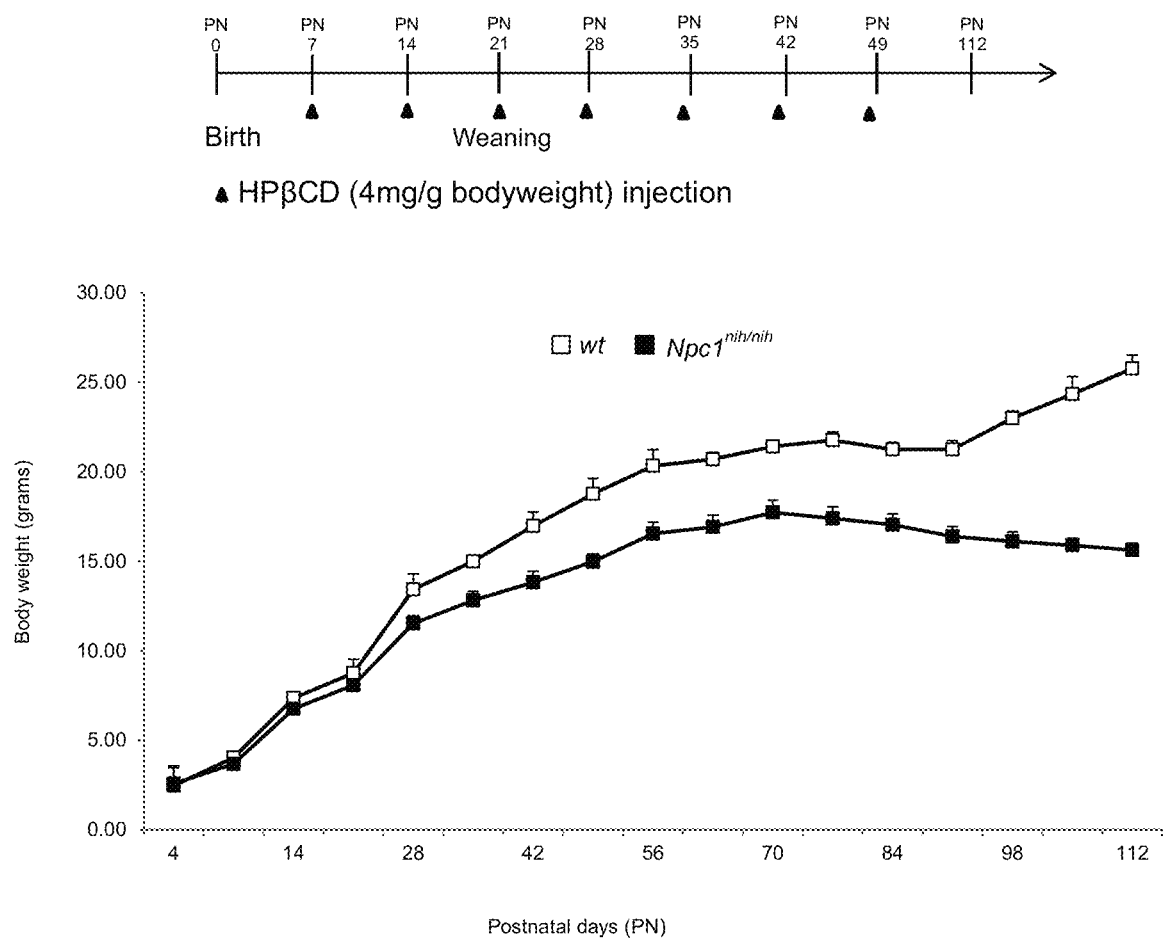
FIG. 10B shows dosing regimen of HPβCD (4 mg/g) in $Npc1^{nih}$ mice compared to WT mice. Body weight of the HPβCD (4 mg/g) treated groups of the study is shown.
Figure 10C:
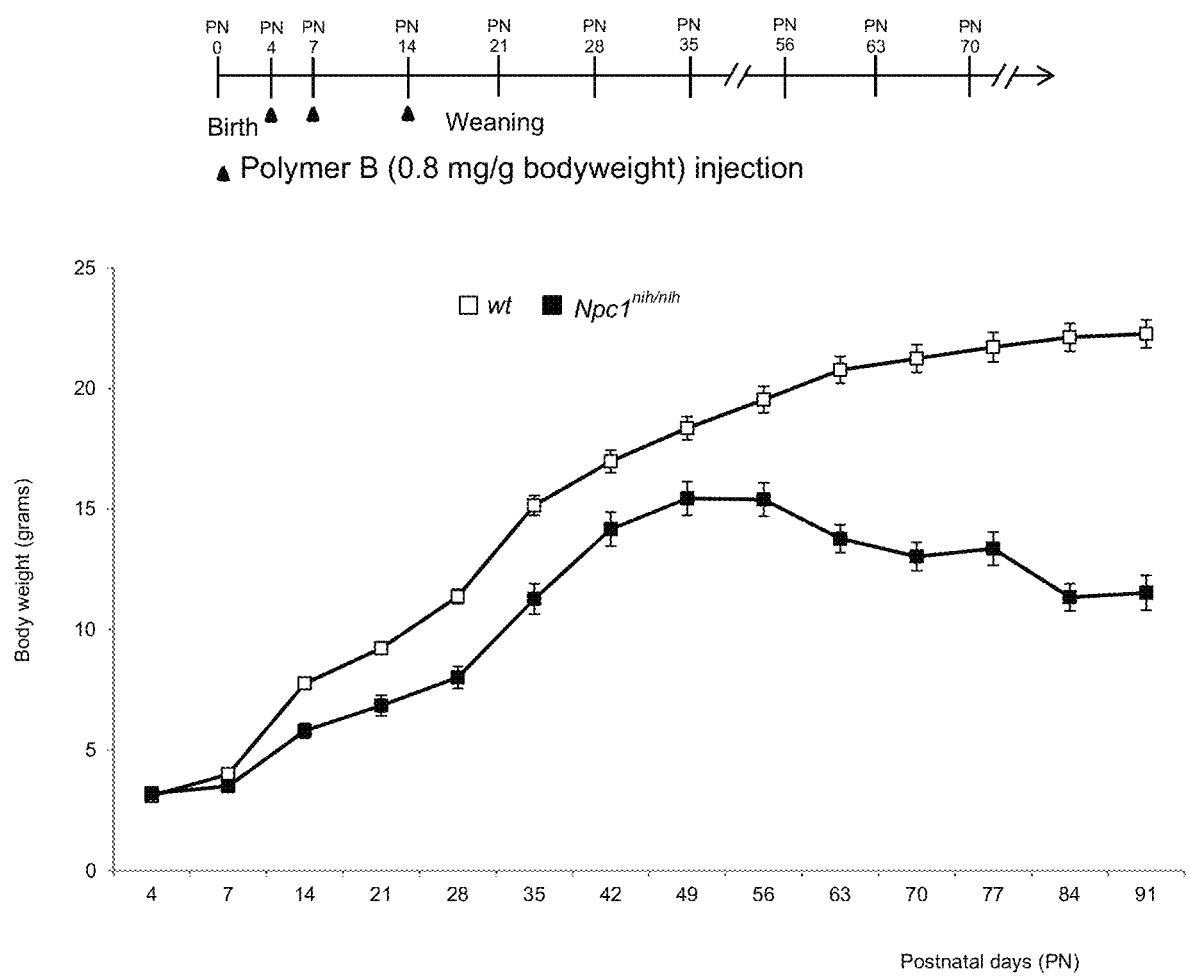
FIG. 10C shows dosing regimen of Polymer B (0.8 mg/g) in $Npc1^{nih}$ mice compared to WT mice. Body weight of the Polymer B (0.8 mg/g) treatment groups is shown.
Figure 11A:
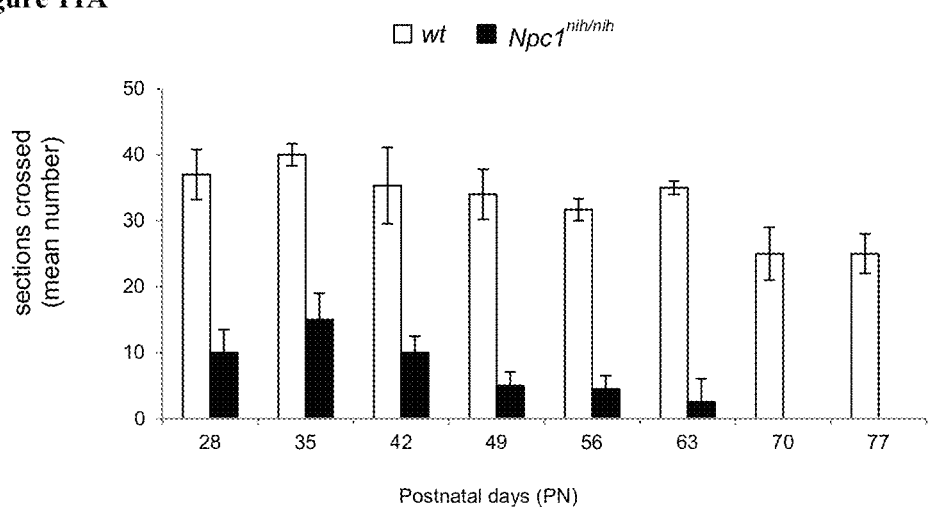
FIG. 11A shows motor behaviour assessment (balance beam test) for the sham PBS WT and $Npc1^{nih}$ mice control groups.
Figure 11B:
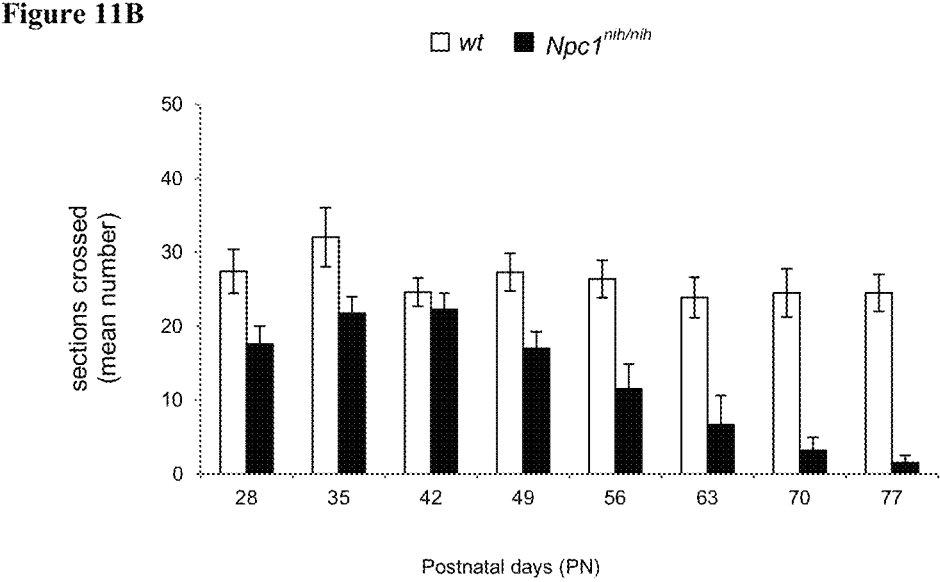
FIG. 11B shows motor behaviour assessment (balance beam test) for the WT and $Npc1^{nih}$ mice group receiving Polymer B (0.8 mg/g).
Figure 23:
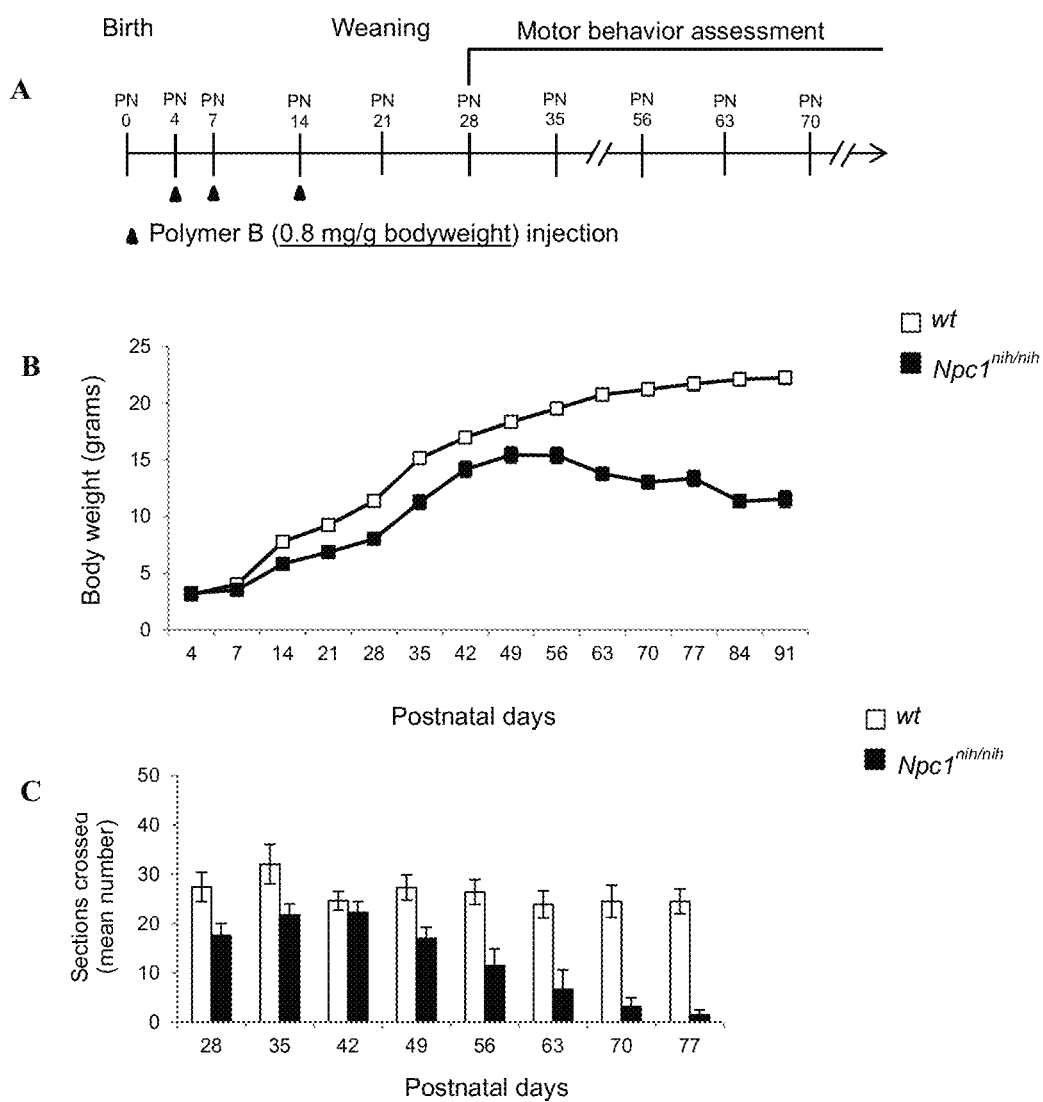
FIG. 23 shows the results of an experiment measuring the body weight and motor skills of WT and $Npc1^{nih}$ mice. A—shows dosing regimen of Polymer B (0.8 mg/g, injections at PN4, PN7, and PN14) in the efficacy studies in $Npc1^{nih}$ mice. B—shows body weight of the WT and Polymer B (0.8 mg/g, injections at PN4, PN7, and PN14) $Npc1^{nih}$ groups. C—shows motor behaviour assessment (balance beam test) for the WT and $Npc1^{nih}$ mice groups treated with Polymer B (0.8 mg/g, injections at PN4, PN7, and PN14). Polymer B treatments stabilize $Npc1^{nih}$ mouse weight loss, and delay the onset of ataxic symptoms.

FIG. 10A-10C shows the dosing regime and weight change of the three mice groups. FIG. 11A-11B shows motor behaviour assessment result in the balance beam test for the control mice and Polymer B mice. Body weight and motor behaviour results are also shown in FIG. 23. The motor behaviour assessment began at PN28. The body weight study and the motor behaviour assessment result together indicate a rescuing efficacy of HPβCD and Polymer B.

Figure 12:
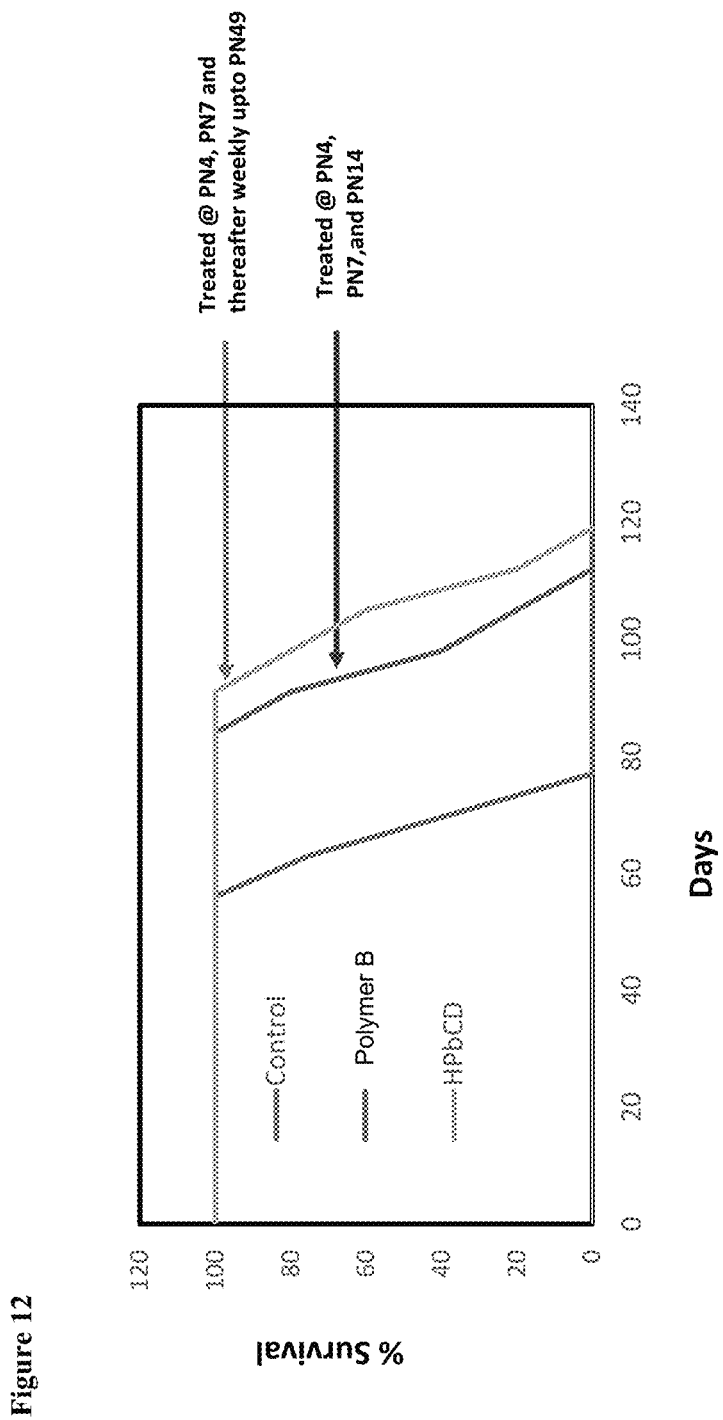
FIG. 12 shows survival rate of the $Npc1^{nih}$ mice in sham PBS control group, HPβCD (4 mg/g) group, and Polymer B (0.8 mg/g) group.

The survival rate of the present study is as shown in FIG. 12. Mice treated with HPβCD survived about 16-17 weeks. Mice treated with Polymer B survived about 14-15 weeks. The control mice survived about 10-11 weeks. This result indicates that Polymer B at lower dosing (0.8 mg/g vs 4 mg/g HPβCD) compared to HPβCD is as efficacious or more efficacious, achieving similar patient outcomes with only 3 injections of Polymer B compared to weekly HPβCD injections at 5× the dose. FIG. 27A also shows the survival rate of mice treated with Polymer B (0.8 mg/g).

Example 6

Efficacy Study in Npc1$^{nih}$ Mouse Models (Polymer A)

Example 5 was repeated for Npc1$^{nih}$ mice receiving Polymer A (0.4 mg/g body weight) via injected (s.c.) weekly starting at PN7 and ending at PN70. The body weight and motor behaviours were analyzed. The results of these analyses were compared to the control mice results from Example 5. Survivability of Npc1$^{nih}$ mice receiving Polymer A (0.4 mg/g body weight) via injected (s.c.) weekly starting at PN7 and ending at PN70 is also shown in FIG. 27B.

Figure 13:
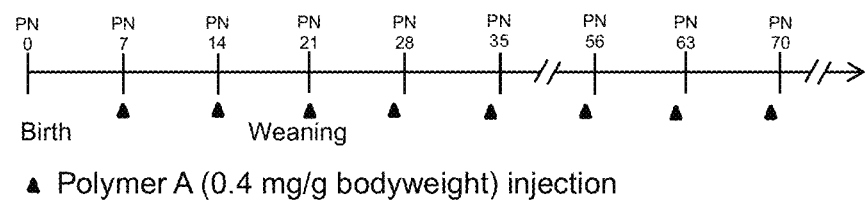
FIG. 13 shows dosing regimen of Polymer A (0.4 mg/g) $Npc1^{nih}$ mice compared to WT mice. Body weight of the Polymer A (0.4 mg/g) treatment groups is shown.
Figure 13:
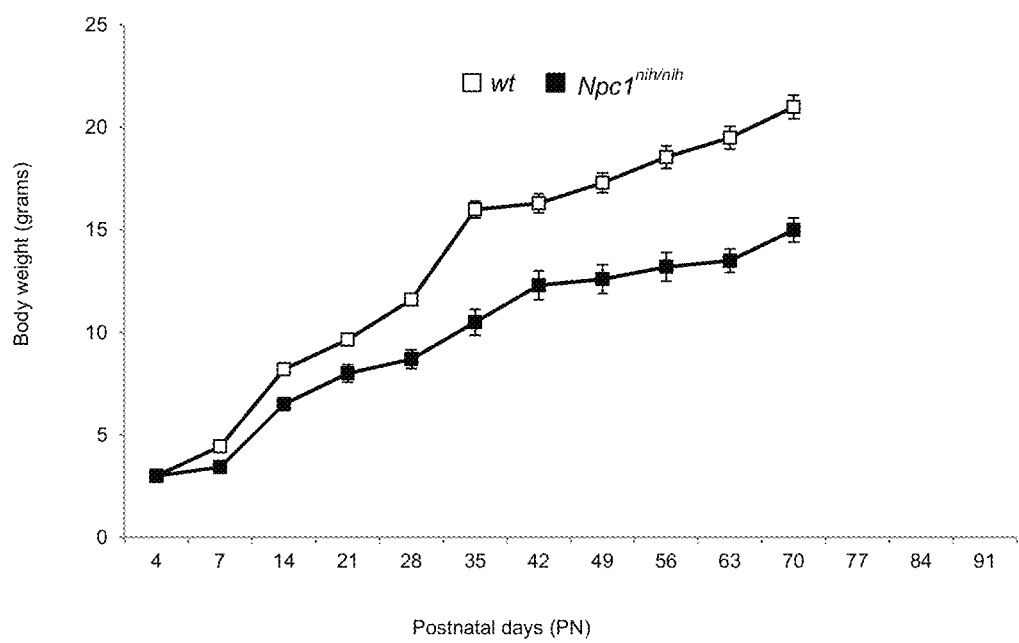
Figure 14:
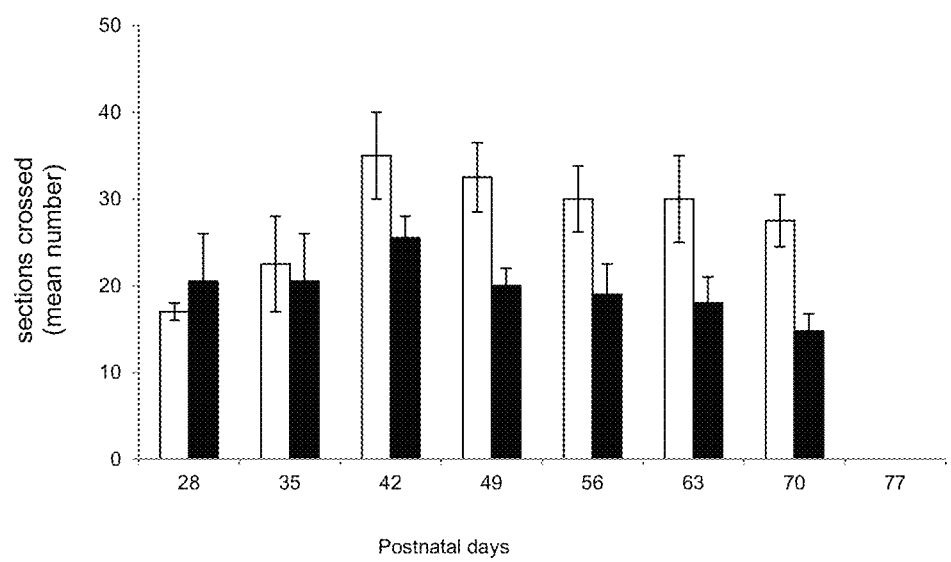
FIG. 14 shows motor behaviour assessment (balance beam test) for the WT, and $Npc1^{nih}$ mice group receiving Polymer A (0.4 mg/g).

No body weight decline was observed with the Npc1$^{nih}$ mice receiving Polymer A (compared to control) indicating a rescuing efficacy of Polymer A (FIG. 13). Also, no decline relative to WT control was observed in the motor behaviour which indicates neuroprotection as demonstrated in the balance beam test (FIG. 14). The dose of Polymer A administered in this test was ⅒ dose of HPβCD in Example 5. This low dosage weekly treatment shows promise as no weight loss is observed at week 10 and the motor abilities are also being preserved. Survival rate will be analysed once the study completes.

Example 7

Efficacy Study in Npc1$^{nmf164}$ Mouse Models (Polymer A)

Npc1$^{nmf164}$ mouse model is a model for a late onset and slower progressing human diseases. This mouse model comprises a single point mutation for a nucleotide change (A/G; D1005G) in the cysteine-rich luminal loop of the Npc1 protein, where many of human mutations occur. This mutation results in loss of functional protein, with protein levels at 10-15% of WT.

Npc1$^{nmf164}$ mice received Polymer A (0.8 mg/g body weight) via injection (s.c.) at the scruff of the neck weekly starting at PN42 (pre-symptomatic study). Another group of Npc1$^{nmf164}$ mice received Polymer A (0.8 mg/g body weight) via injected (s.c.) weekly starting at PN56 (early-symptomatic study). Control mice received PBS (sham). Mean volume of the injection was between 50 to 100 µL according to mice size. The body weight, motor behaviour, and survival rate of each group of mice were analyzed. The results for the pre-symptomatic and early symptomatic treatments were combined into a single experimental treatment.

Figure 15A:
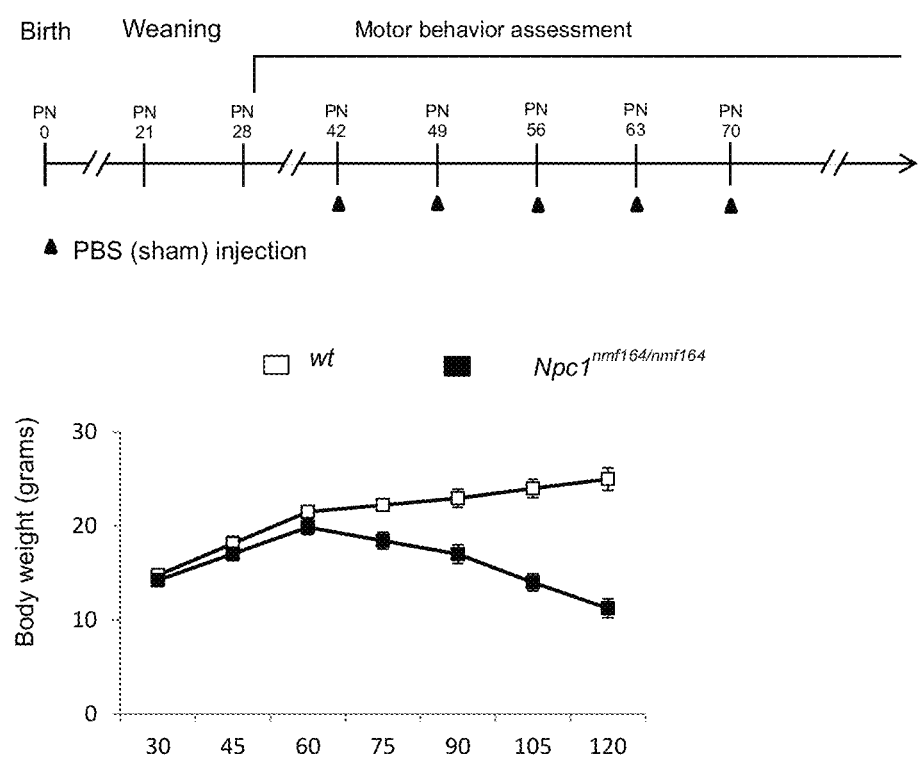
FIG. 15A shows dosing regimen of control group sham PBS injections in the efficacy studies in $Npc1^{nmf164}$ mice. Body weight of the WT and $Npc1^{nmf164}$ control groups is shown. $Npc1^{nmf164}$ mice experience a sharp drop in weight starting at PN60.
Figure 15B:
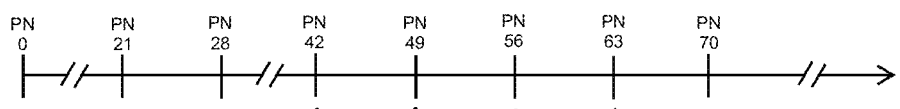
FIG. 15B shows dosing regimen of the Polymer A (0.8 mg/g, pre-symptomatic PN42) and Polymer A (0.8 mg/g, early-symptomatic PN56) groups in the efficacy studies in $Npc1^{nmf164}$ mice. Body weight of the WT and combined Polymer A (0.8 mg/g, early and pre-symptomatic) mice groups is shown. Polymer A pre and early-symptomatic treatments stabilize $Npc1^{nmf164}$ weight loss.
Figure 15B:
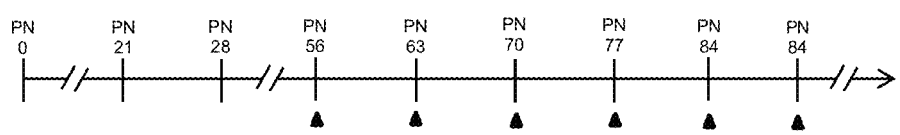
Figure 15B:
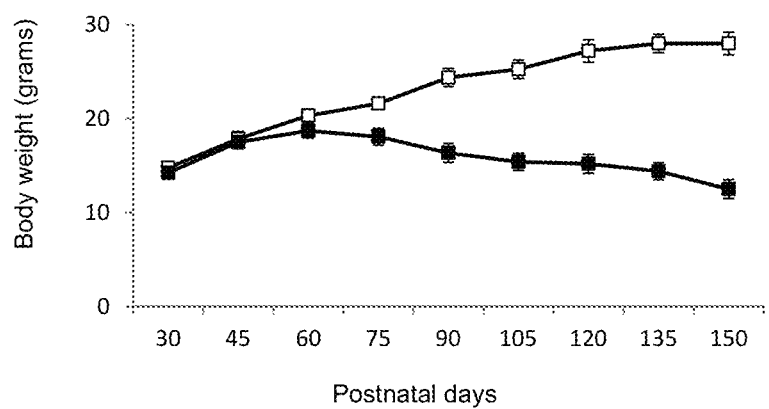
Figure 16A:
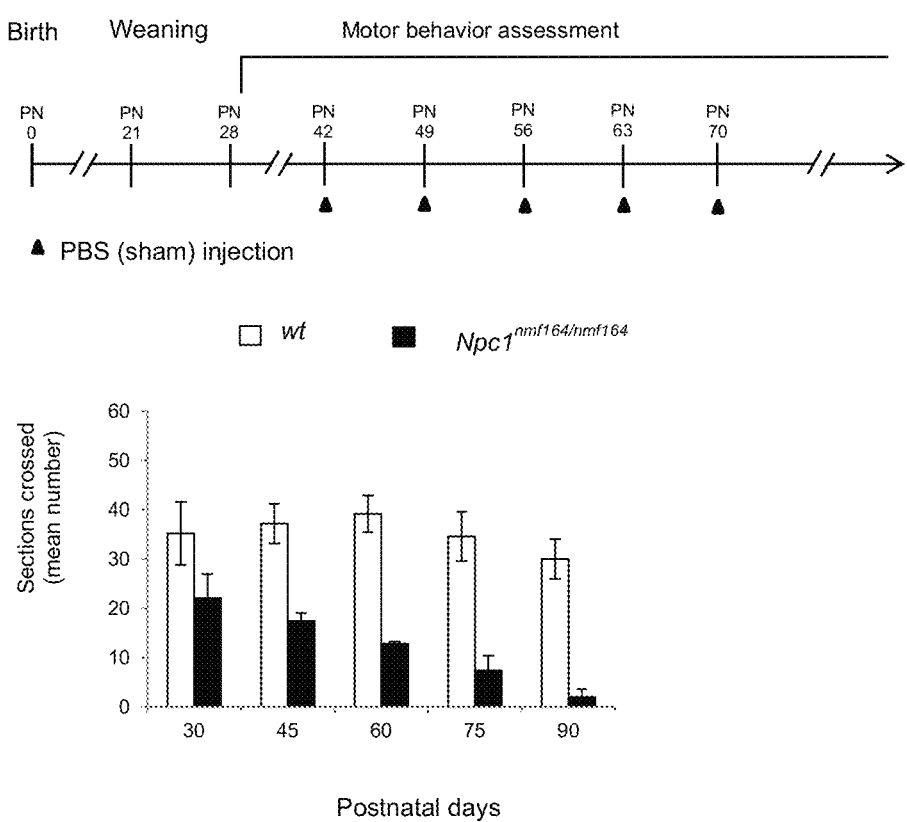
FIG. 16A shows motor behaviour assessment (balance beam test) for the WT, and $Npc1^{nmf164}$ sham mice groups.
Figure 16B:
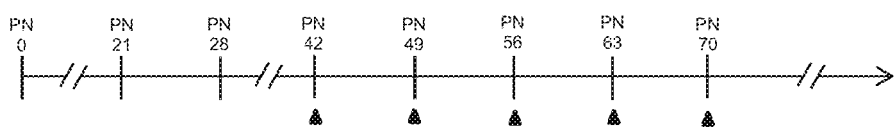
FIG. 16B shows motor behaviour assessment (balance beam test) for the WT, and $Npc1^{nmf164}$ mice treated with Polymer A (0.8 mg/g, pre and early symptomatic combined). Polymer A treatments delay the onset of ataxic symptoms.
Figure 16B:
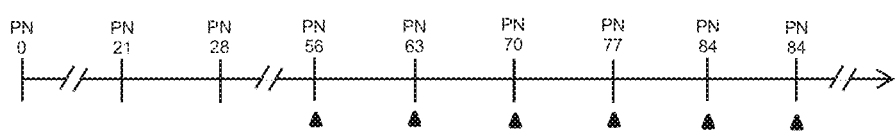
Figure 16B:
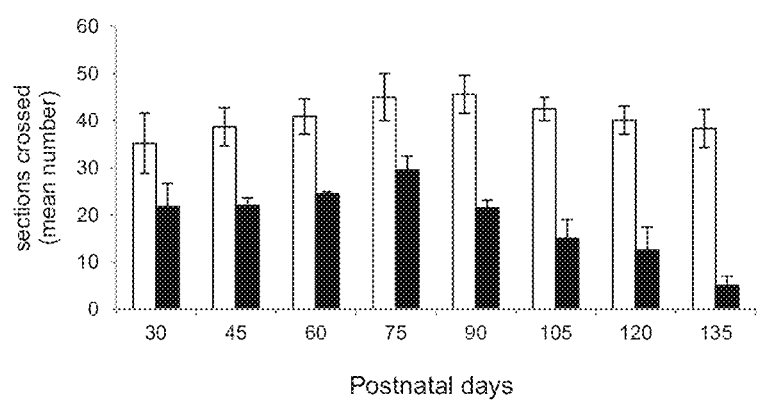

FIGS. 15A-15B shows the dosing regime and weight change of the two remaining groups. FIGS. 16A-16B shows motor behaviour assessment results from the balance beam of the two remaining groups. The weekly injection of Polymer A was effective at treating the mice and shows evidence of delaying onset of symptoms for adult mice.

For example, Polymer A treatment stabilized body weight by attenuating weight loss from Npc1$^{nmf164}$ mice. Polymer A treatment further delayed the onset of ataxic symptoms, which normally appear at PN60 of the PBS sham treatment (compare PN45-90 times showing Polymer A treated mice with significant motor behaviour improvements). Finally, Polymer A treated mice also exhibited mean lifespan from PN120 (Sham) to PN145 (Polymer A).

Figure 17:
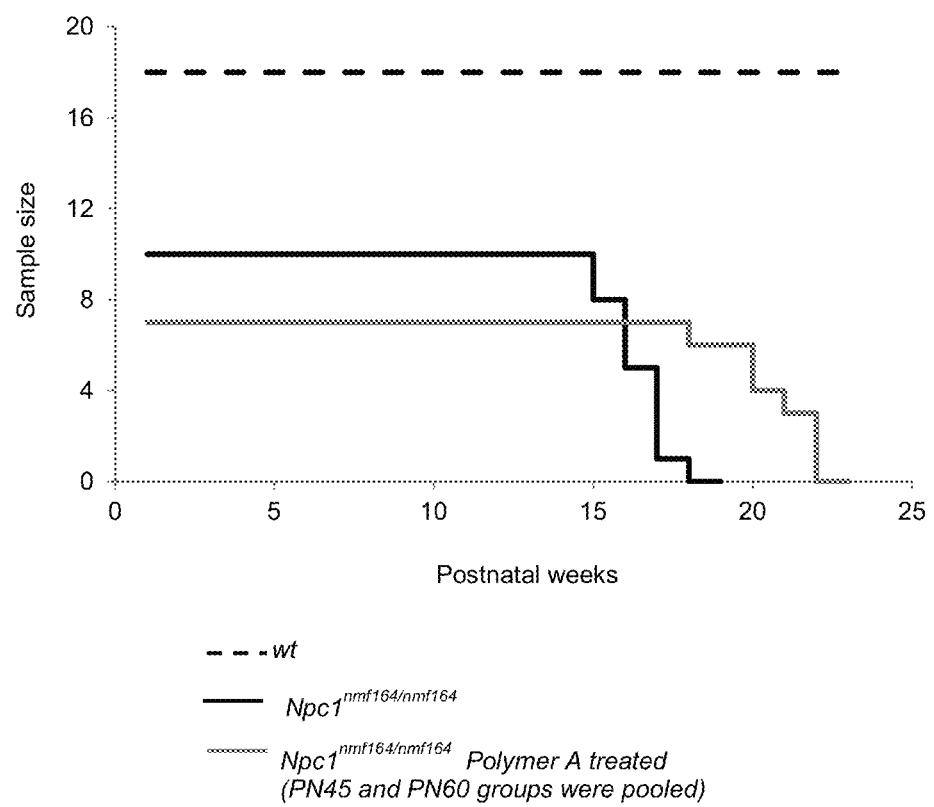
FIG. 17 shows survival rate of the $Npc1^{nmf164}$ mice compared to a WT group, and $Npc1^{nmf164}$ Polymer A (0.8 mg/g, pre and early symptomatic) combined groups. Polymer A pre and early symptomatic treatments extend the life of $Npc1^{nmf164}$ mice.

The survival rate of the present study is as shown in FIG. 17. Npc1$^{nmf164}$ mice treated with Polymer A (0.8 mg/g body weight) via injection (s.c.) survived about 22 weeks compared to untreated mice, which survived about 18 weeks.

Example 8

Intranasal Administration of Polymer A in Mice

Figure 18:
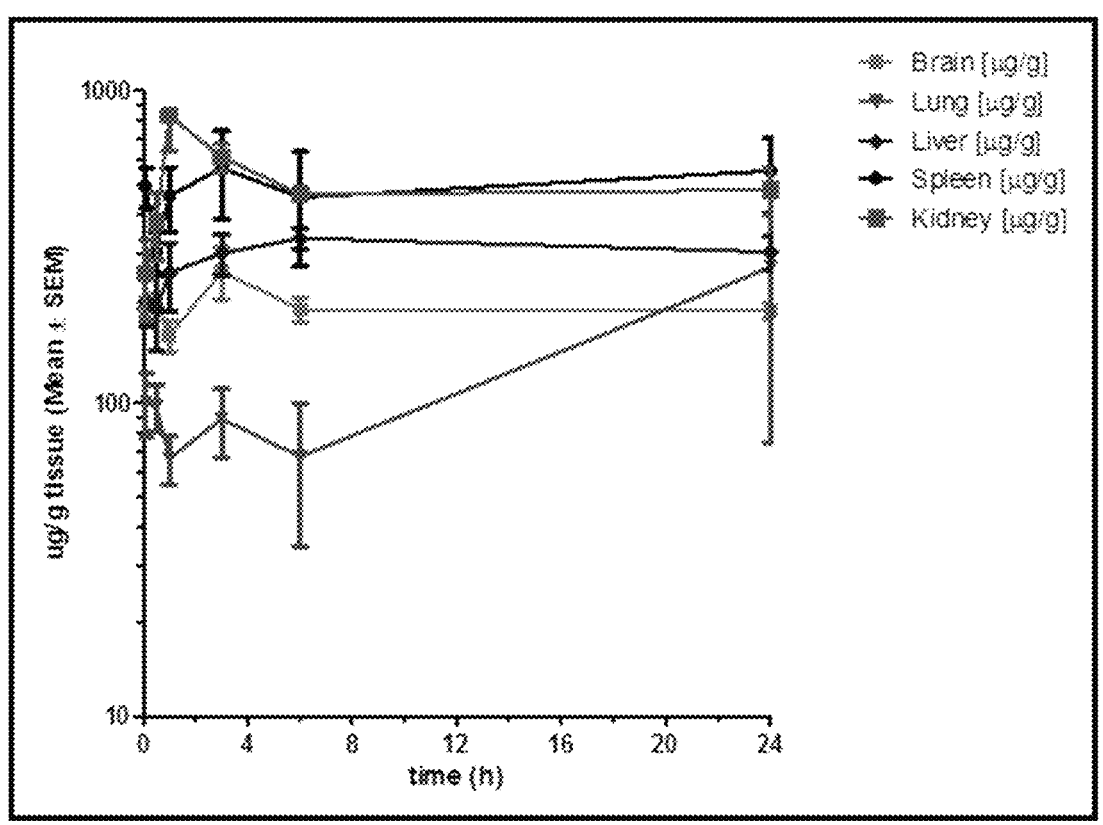
FIG. 18 shows the biodistribution profile of Polymer A in mice treated with the polymer via intranasal administration.

A single intranasal dose of Polymer A (100 mg/kg) was administered to mice. The concentration of Polymer A in various cells was monitored over 24 h. Uptake and retention of Polymer A in various organs was observed (FIG. 18). Four-fold uptake (10-15% i.d.) of Polymer A was observed via intranasal administration in the brain when compared to the s.c. administration over 24 h (Example 3, FIG. 9). Error bars in FIG. 18 are SEM.

Example 9

Comparison of Npc1$^{nmf164}$ Polymer A Dose Size

Different doses for Polymer A treatments were compared in the Npc1$^{nmf164}$ mouse model. Npc1$^{nmf164}$ mice received Polymer A (0.8 mg/g body weight) via injection (s.c.) at the scruff of the neck weekly starting at PN14. Another group of Npc1$^{nmf164}$ mice received Polymer A (0.4 mg/g body weight) via injected (s.c.) weekly starting at PN14. Control mice received PBS sham injections starting at PN14. Mean volume of the injection was between 50 to 100 µL according to mice size. The body weight, motor behaviour, and survival rate of each group of mice were analyzed.

Figure 19A:
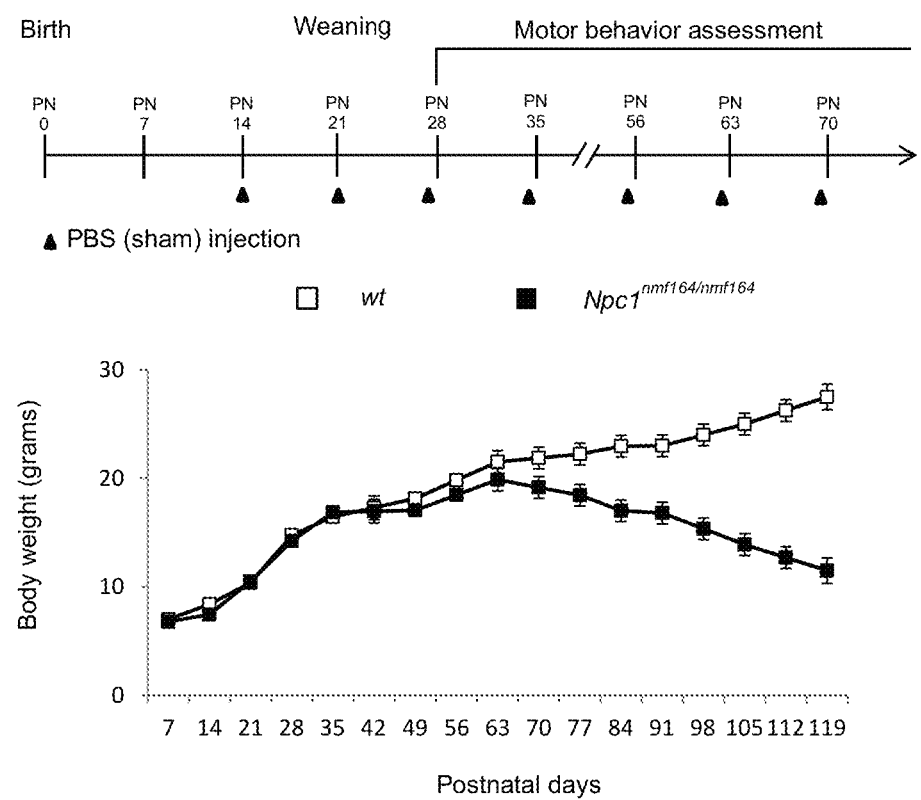
FIG. 19A shows dosing regimen of control group sham PBS injections in the efficacy studies in $Npc1^{nmf164}$ mice. Body weight of the WT and $Npc1^{nmf164}$ control groups is shown. $Npc1^{nmf164}$ mice experience a sharp drop in weight starting at PN60.
Figure 19B:
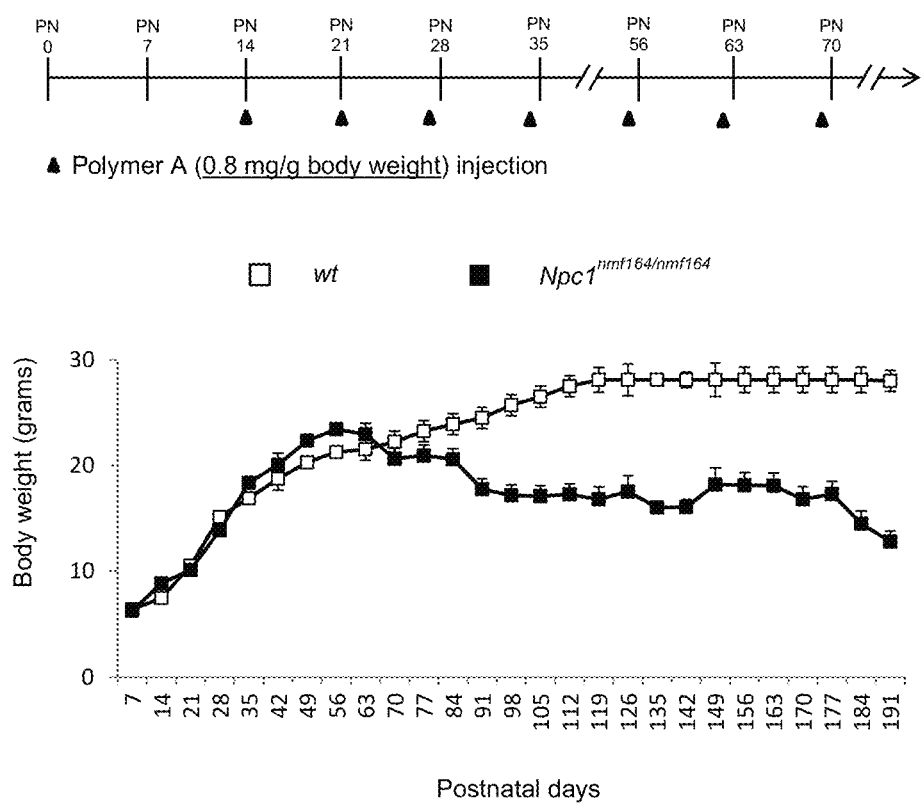
FIG. 19B shows dosing regimen of the Polymer A (0.8 mg/g, weekly injections starting at PN14) group in the efficacy studies in $Npc1^{nmf164}$ mice. Body weight of the WT, and Polymer A (0.8 mg/g, weekly injections starting at PN14) mice groups is shown. Polymer A weekly injection treatment stabilizes $Npc1^{nmf164}$ weight loss.
Figure 19C:
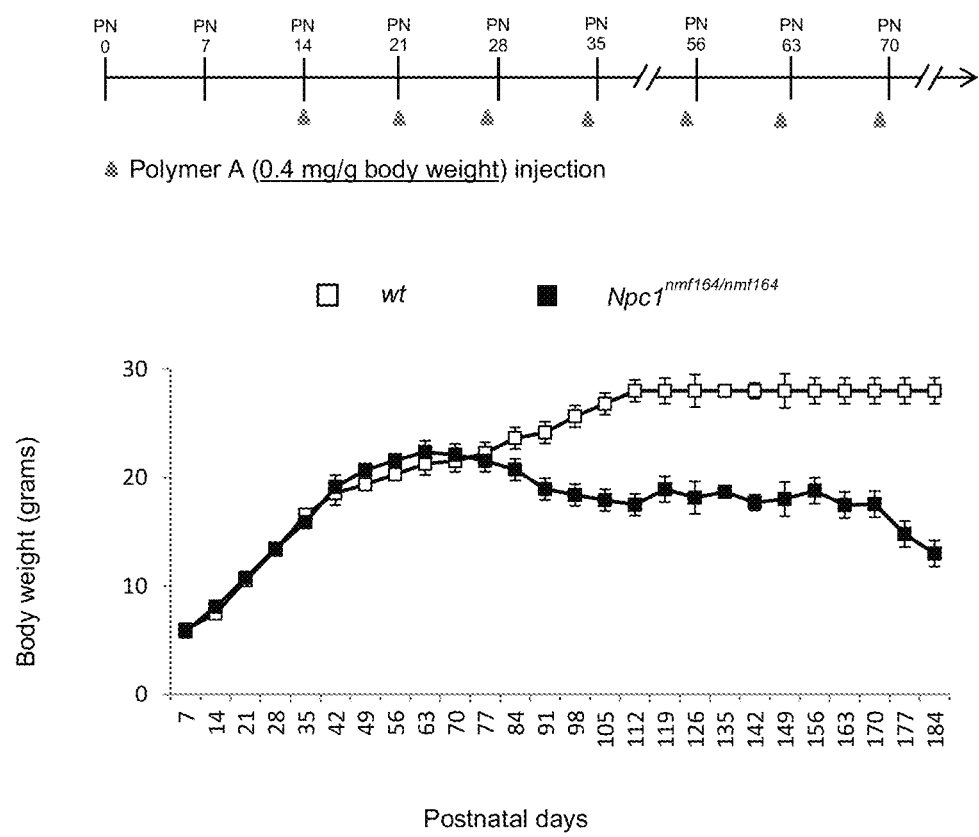
FIG. 19C shows dosing regimen of the Polymer A (0.4 mg/g, weekly injections starting at PN14) group in the efficacy studies in $Npc1^{nmf164}$ mice. Body weight of the WT, and Polymer A (0.4 mg/g, weekly injections starting at PN14) mice groups is shown. Polymer A weekly injection treatment stabilizes $Npc1^{nmf164}$ weight loss.
Figure 20A:
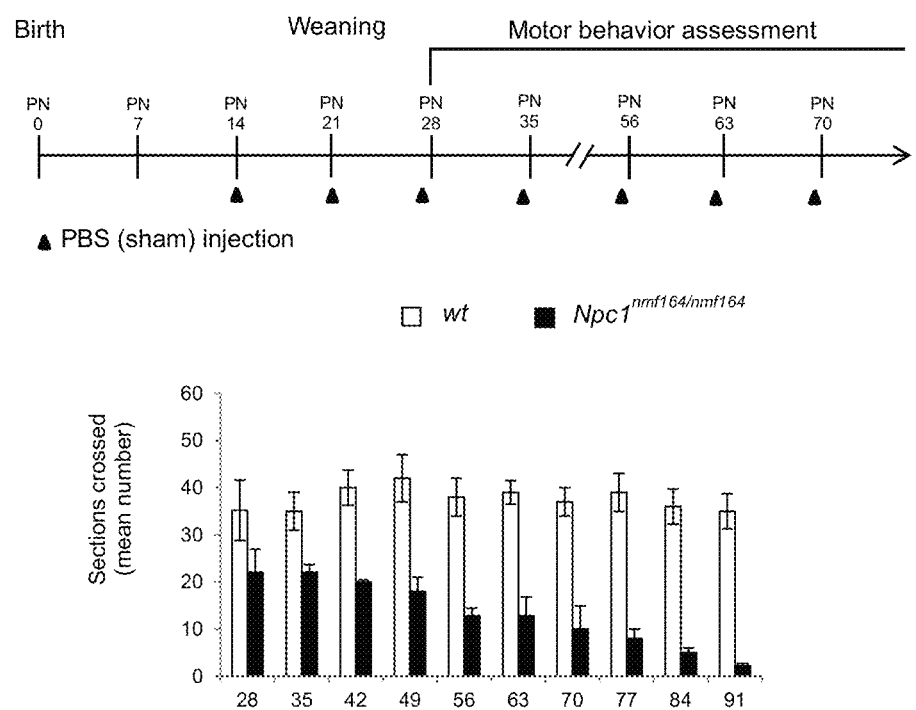
FIG. 20A shows motor behaviour assessment (balance beam test) for the sham treated WT and $Npc1^{nmf164}$ mice groups.
Figure 20B:
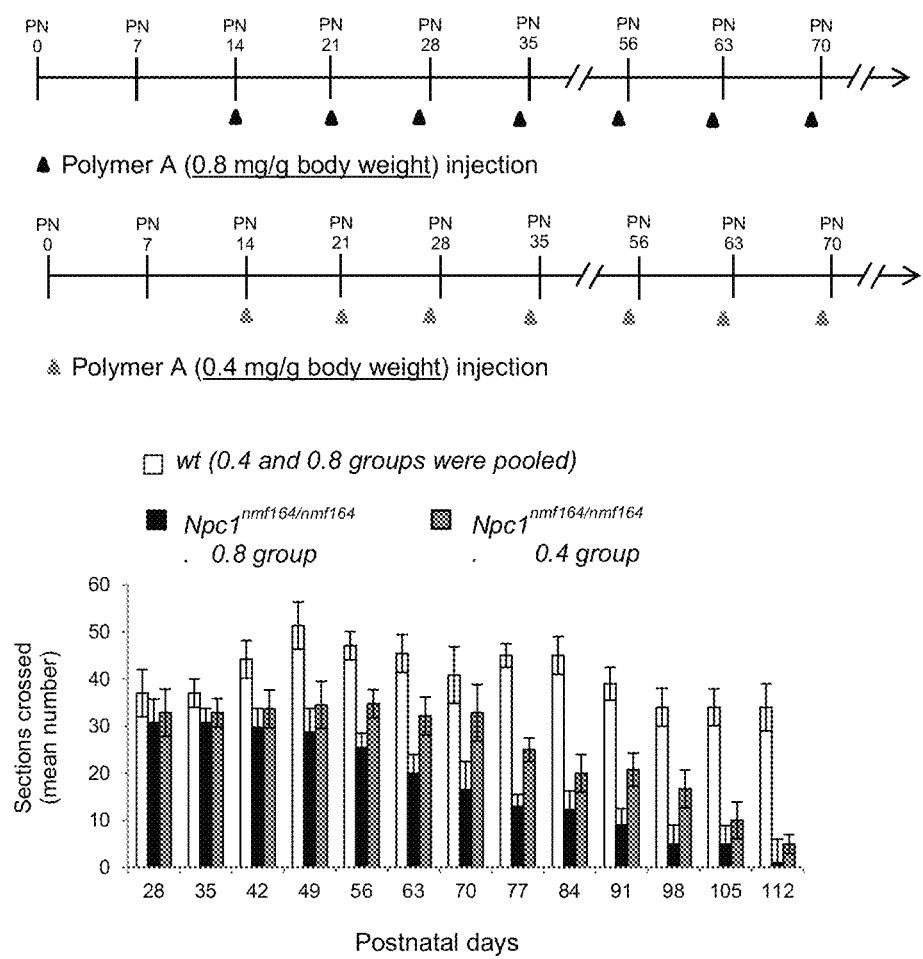
FIG. 20B shows motor behaviour assessment (balance beam test) for WT, and $Npc1^{nmf164}$ mice treated with Polymer A (0.8 mg/g, weekly injections starting at PN14) and Polymer A (0.4 mg/g, weekly injections starting at PN14). Polymer A treatments delay the onset of ataxic symptoms. Lower dosage Polymer A treatment (0.4 mg/g, weekly injections starting at PN14) exhibits similar protective effects as higher dosage treatments.

FIGS. 19A-19C show the dosing regime and weight change of the three groups. FIGS. 20A-20B show motor behaviour assessment results in the balance beam of the three groups. The results demonstrate that lower Polymer A doses of (0.4 mg/g body weight) can produce similar protective effects as the higher Polymer A (0.8 mg/g body weight) doses on body weight and motor behaviour.

Figure 21:
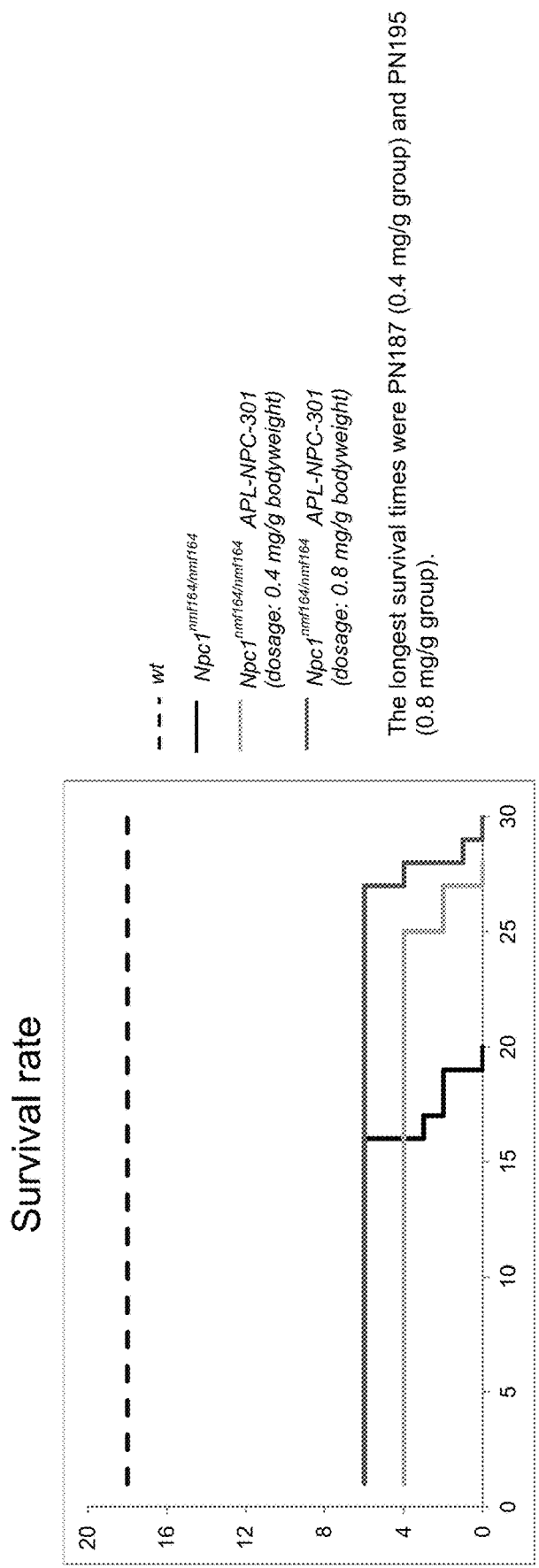
FIG. 21 shows survival rate of WT mice compared to $Npc1^{nmf164}$ mice with PBS treatments, $Npc1^{nmf164}$ Polymer A (0.4 mg/g weekly injections starting at PN14), and $Npc1^{nmf164}$ Polymer A (0.8 mg/g weekly injections starting at PN14).

The survival rate of the present study is as shown in FIG. 21. The longest survival times were PN187 (0.4 mg/g group) and PN195 (0.8 mg/g group). A similar study conducted with nmf164 mice treated with 4000 mg/kg of 2-hydroxypropyl-b-cyclodextrin showed median survival of 175-185 days (Haldar et al., 2016 Sci. Transl Med. Vol 8: 326).

Example 10

Determining the Efficiency of Various Cyclodextrin Polymer Treatments on Npc1$^{nih}$ Mice The effects of various cyclodextrin polymers, doses, and injection schedules were tested on Npc1$^{nih}$ mice. A first treatment group of WT and Npc1$^{nih}$ mice received Polymer B (0.4 mg/g body weight) via injection (s.c.) at the scruff of the neck for three weeks at PN4, PN7, and PN14. A second treatment group of WT and Npc1$^{nih}$ mice received Polymer A (0.4 mg/g body weight) via injected (s.c.) weekly starting at PN7. A third treatment group of WT and Npc1$^{nih}$ mice received Polymer A (0.8 mg/g body weight) via injected (s.c.) weekly starting at PN7. A fourth treatment group of WT and Npc1$^{nih}$ mice received Polymer A (0.8 mg/g body weight) via injected (s.c.) weekly starting at PN14. Control mice received PBS sham injections starting at PN7. Mean volume of the injection was between 50 to 100 µL according to mice size. The body weight, motor behaviour, and survival rate of each group of mice were analyzed.

Figure 22:
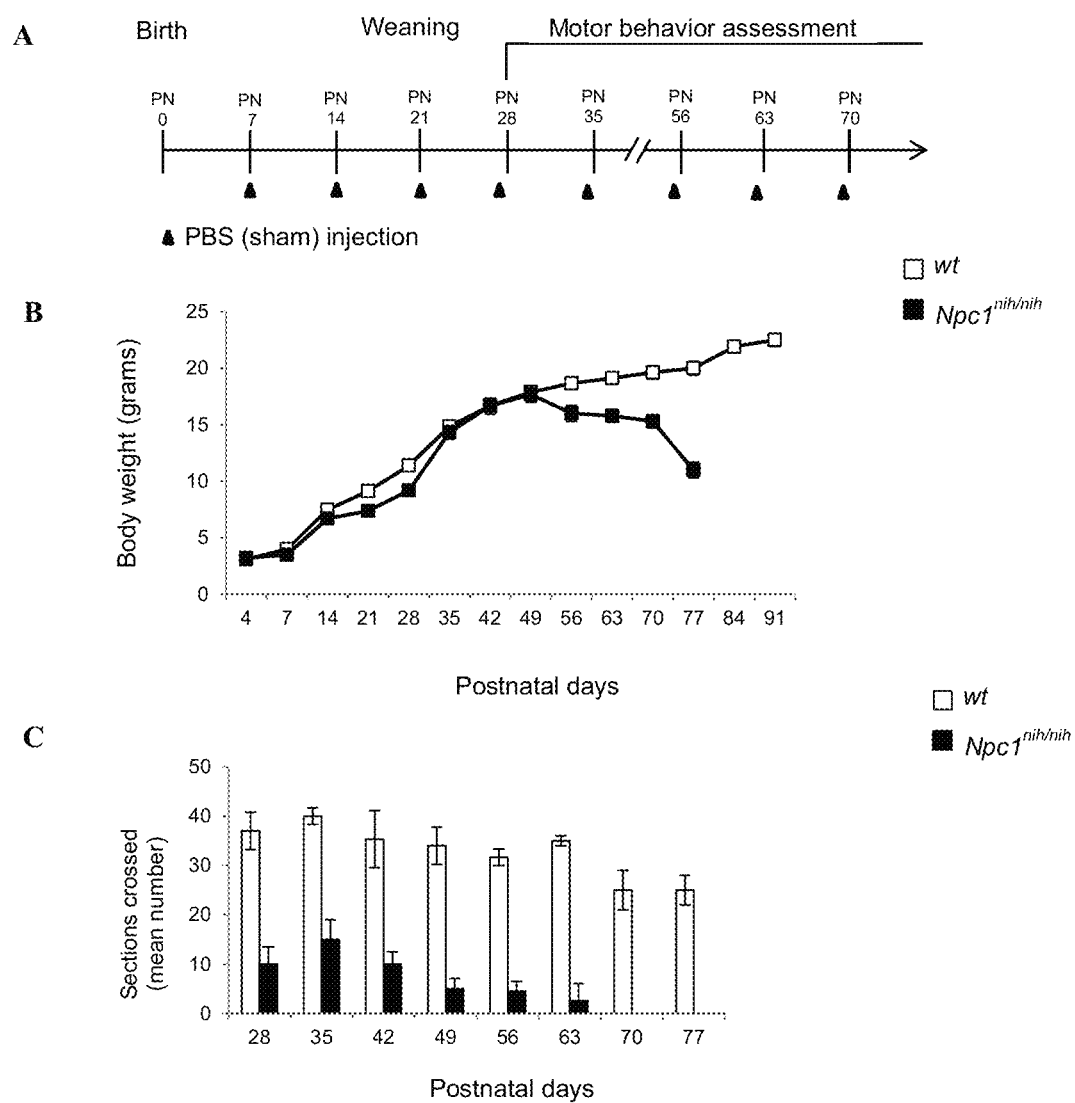
FIG. 22 shows the results of an experiment measuring the body weight and motor skills of $Npc1^{nih}$ mice. A—shows dosing regimen of control group sham PBS injections in the efficacy studies in WT and $Npc1^{nih}$ mice. B—shows body weight of the WT and $Npc1^{nih}$ control groups. C—shows motor behaviour assessment (balance beam test) for the WT and $Npc1^{nih}$ mice groups. $Npc1^{nih}$ mice experience a sharp drop in weight starting at PN49.
Figure 24:
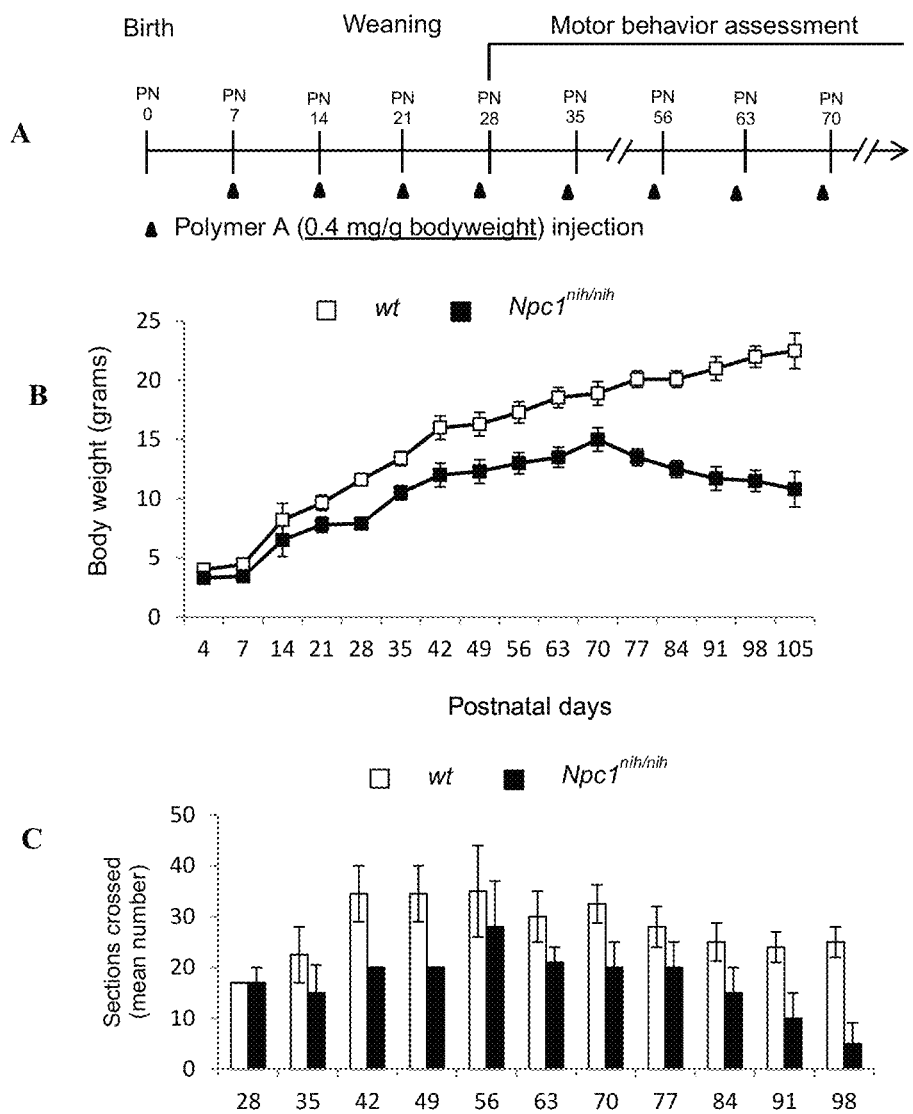
FIG. 24 shows the results of an experiment measuring the body weight and motor skills of WT and $Npc1^{nih}$ mice. A—shows dosing regimen of Polymer A (0.4 mg/g, weekly injections starting at PN7) in the efficacy studies in $Npc1^{nih}$ mice. B—shows body weight of the WT and Polymer A (0.4 mg/g, weekly injections starting at PN7) $Npc1^{nih}$ groups.

FIGS. 22A-C show the dosing regime, weight change, and motor behaviour results for the control PBS sham control treatment group. FIGS. 23A-C show the dosing regime, weight change, and motor behaviour results for the Polymer B (0.8 mg/g body weight, PN4, PN7, PN14) treatment group. FIGS. 24A-C show the dosing regime, weight change, and motor behaviour results for the Polymer A (0.4 mg/g body weight weekly injection starting at PN7) treatment group. FIGS. 25A-C show the dosing regime, weight change, and motor behaviour results for the Polymer A (0.8 mg/g body weight weekly injection starting at PN7) treatment group. FIGS. 26A-C show the dosing regime, weight change, and motor behaviour results for the Polymer A (0.8 mg/g body weight weekly injection starting at PN14) treatment group.

The results demonstrate that each of the cyclodextrin polymer doses is safe, as no detrimental effect is seen in any of the WT mice. The results also surprisingly showed that lower Polymer A doses of (0.4 mg/g body weight) produced significantly better motor behaviour results for Npc1$^{nih}$ mice than their higher Polymer A (0.8 mg/g body weight) dose counterparts. Indeed Npc1$^{nih}$ mice treated with Polymer A doses of (0.4 mg/g body weight) retained significant motor behaviour past PN91, whereas untreated controls lost all motor behaviour after PN63, and Polymer A doses of (0.8 mg/g body weight) exhibited almost a complete loss at PN84. The survival rate of the present study is as shown in FIG. 27.

Example 11

Determining the Half-Life of Cyclodextrin Polymer Administrations in Mice

The effects of various cyclodextrin polymers were tested on WT mice. WT mice were injected with a single subcutaneous dose of 500 mg/kg of HPbCD, Polymer A, or Polymer B. PK measurements were taken every 2 hours via HPLC-UV measurements of mouse plasma. FIG. 28 presents the half-life results of this experiment. Polymer A and Polymer B exhibited improved half-lives compared to HPBCD. The recovery was 90% from plasma and tissues. Bioavailability calculations resulted in a 42% bioavailability for HPbCD, 62% bioavailability for Polymer A, and 100% bioavailability for Polymer B.

Additional embodiments and features of the present disclosure will be apparent to one of ordinary skill in art based upon description and examples provided herein. However, the examples below should not be construed to limit the scope of the present disclosure.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments in this disclosure have been described in terms of different embodiments, those skilled in the art will recognize that the embodiments herein can be practiced with modification within the spirit and scope of the embodiments as described herein.

Thus, the present disclosure introduces polymers of cyclodextrin conjugates, particularly pbCDK polymers, corresponding methods and applications wherein said polymers possess improved properties including but not limiting to longer circulation time, prolonged duration of action, improved biocompatibility, improved efficacy for removing cholesterol from the cells/treating lipid storage disorders, ease of administration/effective route of administration leading to increased patient compliance, increased uptake in the brain leading to higher neuroprotection efficacy, lower doses, lower number of administrations of the polymer or composition thereof, and lower side effects.

The publications discussed herein are provided solely for their disclosure prior to the filing date of the present application. Nothing herein is to be construed as an admission that the present invention is not entitled to antedate such publication by virtue of prior invention.

While the invention has been described in connection with proposed specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

We claim:
1. A polymer comprising the following structure:

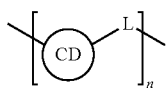

wherein:
CD is a cyclodextrin moiety;
L is a linker moiety having the structure:

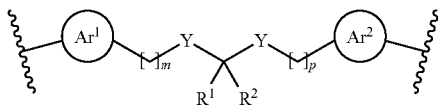

wherein:
Ar$^1$ and Ar$^2$ are each independently a 5- or 6-membered heteroaryl comprising 1, 2, 3 or 4 heteroatoms individually selected from N, O, and S, wherein Ar$^1$ and Ar$^2$ are optionally substituted with R$^3$;

each Y is independently O, S, or NR$^4$;

m and p are each independently an integer from 1 to 10;

R$^1$ and R$^2$ are each independently R$^4$, OR$^4$, S, or R$^1$ and R$^2$ together form a double bonded O, S, or NR$^4$;

R$^3$ is selected from C$_1$-C$_3$ alkyl, C$_1$-C$_3$ alkyl sulphide, hydrazine, amine and halogen;

R$^4$ is H or a saturated or unsaturated C$_1$-C$_{10}$ linear alkyl, saturated or unsaturated C$_1$-C$_{10}$ branched alkyl, or saturated or unsaturated C$_1$-C$_{10}$ cycloalkyl, each of which is optionally substituted; and n is from 4 to 1000.

2. The polymer of claim 1, wherein the cyclodextrin moiety is prepared by polymerizing a cyclodextrin selected from the group consisting of α-cyclodextrin, β-cyclodextrin, γ-cyclodextrin, derivatives thereof, and combinations thereof.

3. The polymer of claim 2, wherein the cyclodextrin moiety is prepared by polymerizing a cyclodextrin selected from the group consisting of hydroxyalkyl-α-cyclodextrin, hydroxyalkyl-β-cyclodextrin, hydroxyalkyl-γ-cyclodextrin, β-cyclodextrin, (2-hydroxypropyl)-β-cyclodextrin, derivatives thereof, a salt thereof, a solvate thereof, and combinations thereof.

4. The polymer of claim 3, wherein alkyl is selected from C$_1$-C$_{10}$ linear alkyl, C$_1$-C$_{10}$ branched alkyl and C$_1$-C$_{10}$ cycloalkyl, each having one or more optional substituents.

5. The polymer of claim 4, wherein the one or more optional substituents are selected from methyl, ethyl and butyl.

6. The polymer of claim 1, wherein Y is O, Ar$^1$ and Ar$^2$ are each triazole, and R$^3$ is C$_1$-C$_3$ alkyl.

7. The polymer of claim 1, wherein m and p are both 1.

8. The polymer of claim 1, wherein R$^1$ and R$^2$ are each C1-C3 alkyl.

9. The polymer of claim 1, wherein L is

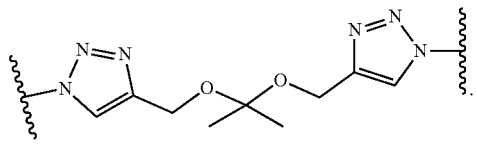 [SMILES: *n1cc(COC(C)(C)OCc2cn(*)nn2)nn1]

10. The polymer of claim 1, wherein the polymer has the following structure:

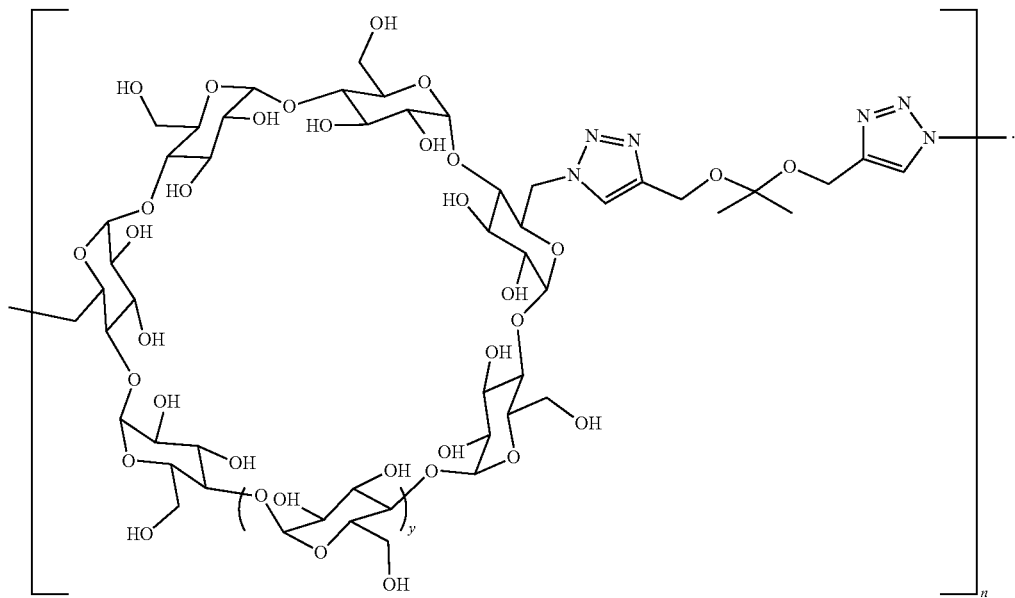

11. The polymer of claim 10, wherein n is from 10 to 300.

12. The polymer of claim 10, wherein n is from 15 to 65.

13. A pharmaceutical composition comprising a pharmaceutically acceptable carrier or a pharmaceutical excipient and the polymer of claim 1.

14. The pharmaceutical composition of claim 13, further comprising a therapeutically active agent.

15. A method of treating a disease or a condition associated with abnormal NPC1 and/or NPC2 protein production, comprising administering to a subject in need thereof the polymer of claim 1.

16. A method of treating lipid storage disorder, comprising administering to a subject in need thereof the polymer of claim 1.

17. A method of treating Niemann-Pick disease, comprising administering to a subject in need thereof the polymer of claim 1.

18. The polymer of claim 1, wherein the polymer has a polydispersity index of from about 1 to about 1.8 and the polymer has an elimination half-life from about 6 hours to about 24 hours.

19. The pharmaceutical composition of claim 14, wherein the bioavailability of the therapeutically active agent is improved and permeation of the blood-brain barrier of the therapeutically active agent is improved.

20. The pharmaceutical composition of claim 14, wherein the therapeutically active agent is paclitaxel, camptothecin, voriconazole, cyclosporin A, doxorubicin, or combinations thereof.

* * * * *